(12) United States Patent
Hagiwara

(10) Patent No.: US 12,410,395 B2
(45) Date of Patent: Sep. 9, 2025

(54) CELL TREATMENT AGENT

(71) Applicant: Nagase ChemteX Corporation, Osaka (JP)

(72) Inventor: Akeo Hagiwara, Shiga (JP)

(73) Assignee: Nagase ChemteX Corporation, Osaka (JP)

( * ) Notice: Subject to any disclaimer, the term of this patent is extended or adjusted under 35 U.S.C. 154(b) by 464 days.

(21) Appl. No.: 17/802,478

(22) PCT Filed: Feb. 27, 2021

(86) PCT No.: PCT/JP2021/007587
§ 371 (c)(1),
(2) Date: Aug. 25, 2022

(87) PCT Pub. No.: WO2021/172579
PCT Pub. Date: Sep. 2, 2021

(65) Prior Publication Data
US 2023/0098630 A1    Mar. 30, 2023

(30) Foreign Application Priority Data

Feb. 28, 2020 (JP) ................................ 2020-034264
Oct. 21, 2020 (JP) ................................ 2020-176560

(51) Int. Cl.
*C12N 5/00* (2006.01)

(52) U.S. Cl.
CPC ......... *C12N 5/0068* (2013.01); *C12N 5/0018* (2013.01); *C12N 2533/74* (2013.01); *C12N 2539/10* (2013.01)

(58) Field of Classification Search
None
See application file for complete search history.

(56) References Cited

U.S. PATENT DOCUMENTS

| 2015/0011003 A1 | 1/2015 | Kuriyama et al. |
| 2015/0329832 A1 | 11/2015 | Senda et al. |

FOREIGN PATENT DOCUMENTS

| JP | 2002-536974 A | 11/2002 | |
| WO | 0049135 A2 | 8/2000 | |
| WO | 2013147264 A1 | 10/2013 | |
| WO | WO-2014072035 A1 * | 5/2014 | ........... A01N 1/0231 |
| WO | 2014119219 A1 | 8/2014 | |

OTHER PUBLICATIONS

Araújo, et al. Selective sulfation of carrageenans and the influence of sulfate regiochemistry on anticoagulant properties. Carbohydrate Polymers. 91(2013)483-91. (Year: 2013).*
Crapo, Peter M. et al., "An overview of tissue and whole organ decellularization processes", Biomaterials 32, 3233-3243 (2011).
Hayflick, Leonard et al., "Subculturing Human Diploid Fibroblast Cultures", Edited by Kruse, P. F., et al., Tissue Culture Methods and Applications. 220-223 Academic Press (New York) (1973).
Yamato, Masayuki et al., "Thermo-Responsive Culture Dishes Allow the Intact Harvest of Multilayered Keratinocyte Sheets without Dispase by Reducing Temperature", Tissue Engineering, 7, 473-480 (2001).
Dorantes-Aranda, Juan Jose et al., "Novel application of a fish gill cell line assay to assess ichthyotoxicity of harmful marine microalgae", Harmful Algae., 10, 366-373 (2011).
Liang, Chao et al., "Serotonin promotes the proliferation of serum-deprived hepatocellular carcinoma cells via upregulation of FOXO3a", Molecular Cancer 12 (2013) (open access).
Schulz, Julia C. et al., "Towards a xeno-free and fully chemically defined cryopreservation medium for maintaining viability, recovery, and antigen-specific functionality of PBMC during long-term storage", Journal of Immunological Methods, 382, 24-31 (2012).
Berven, Lise et al., "Alginates induce legumain activity in RAW 264.7 cells and accelerate autoactivation of prolegumain", Bioactive Carbohydrates and Dietary Fibre, 2013, vol. 2, pp. 30-44, fig. 3.

* cited by examiner

*Primary Examiner* — Allison M Fox
*Assistant Examiner* — Gina Pronzati
(74) *Attorney, Agent, or Firm* — Troutman Pepper Locke LLP; James E. Armstrong, IV; Nicholas J. DiCeglie, Jr.

(57) ABSTRACT

A cell treatment agent containing alginate sulfate as an active ingredient, and a set reagent for activating suspended or dormant cells, which is a combination reagent of the cell treatment agent and an activator containing polyvalent cations are provided.

10 Claims, 4 Drawing Sheets

CELL TREATMENT AGENT

CROSS-REFERENCE TO RELATED APPLICATIONS

This application is a U.S. national phase application filed under 35 U.S.C. § 371 of International Application No. PCT/JP2021/007587, filed Feb. 27, 2021, which is based upon and claims the benefit of priority from prior Japanese Application No. 2020-034264, filed Feb. 28, 2020, and prior Japanese Application No. 2020-176560, filed Oct. 21, 2020.

TECHNICAL FIELD

The present invention relates to a cell treatment agent, in particular, a cell treatment agent that is used in performing treatments of detaching and suspending cells, making cells dormant, maintaining viability, preventing death, and activating suspended or dormant cells, for cells in tissue of, for example, an organ or tissues of a living body, or cultured cells.

BACKGROUND ART

In survival and proliferation of adherent cells that are the majority of cells (hereinafter simply referred to as "cells") except for special cells (non-adherent cells) such as unicellular organisms, blood cells, and cancer cells, the cells survive, exert their functions, and proliferate while they adhere to a scaffold of an extracellular matrix constituting a body in the body, or a scaffold such as a wall of a culture vessel or a predetermined carrier in a culture substrate. When such cells are used for research or medical care, it is necessary to detach the cells from the scaffold and suspend the cells without weakening the cells.

In operations of detaching and suspending the cells, it is common to utilize the cell detaching effect of a surfactant or a cell detachment enzyme such as trypsin. For example, for collection of only cells by detaching and suspending the cells from a living organ, there has been known a treatment method that includes digesting a component that makes the cells adhere to the scaffold with a cell detachment agent such as a cell detachment enzyme or a surfactant to detach and suspend the cells, and collecting the cells by washing out the cells from the living organ (see NPL 1 for a surfactant method using a surfactant). For detaching cells in culture from a predetermined scaffold, and suspending the cells, there has been known a treatment method of adding a liquid containing a cell detachment agent such as trypsin to the culture vessel to cause the cell detachment agent to act on the cultured cells, thus detaching and suspending the cells (NPL 2).

However, surfactants and cell detachment enzymes used in these detaching and suspending treatments also digest essential components of the cells themselves. Therefore, if the surfactant or the cell detachment enzyme continuously acts on the cells even after detachment and suspension, the suspended cells will weaken and eventually die. Thus, the surfactant or the cell detachment enzyme has cytotoxicity. In order to protect suspended cells from the cytotoxicity, the suspended cells are separated from the surfactant or the cell detachment enzyme after suspending the cells, or the separated cells are washed or the surfactant or the enzyme is inactivated to remove the cytotoxic effect of the surfactant or the cell detachment enzyme. However, such a treatment using a cell detachment agent having cytotoxicity is inevitably accompanied by cell death to a certain extent in the course of suspension. Also, in order to use suspended cells for research or medical care, it is required to maintain viability without weakening the cells during detachment and suspension.

In light of such a current situation, there has been developed a method of using a special polymer as a temperature-sensitive cell culture scaffold and heating a part of the polymer to a certain temperature to detach and suspend cells (NPL 3). However, high price due to use of a special polymer, need of a special temperature control device, difficulty in temperature control or the like and unstable result, unusability in a stereoscopic and complicated device for culturing a large amount of cells, impossibility to detach and suspend cells in tissue from a living organ, and the like have been pointed out for this method.

When cells are used for research or medical care, it is necessary to store and transport the cells safely. In such a case, cells are generally transported and stored while they are contained in a liquid for preservation and transportation (preservation and transportation liquid). Since the cells weaken hourly at room temperature (normal temperature), they are stored and transported in a refrigerated or frozen state, and returned to normal temperature before use.

Even in the refrigerated state or in the course of returning to normal temperature, the viability of the cells decreases and the cells die with time. For the purpose of cell protection to prevent cell death and maintain cell viability, a method of adding and mixing 10% fetal bovine serum (FBS) or autologous serum to the liquid for preserving and transporting cells has been conventionally performed. It is known that the viability of the cells is dramatically increased (cell protective effect) by mixing fetal bovine serum (FBS) or autologous serum, compared to the case where FBS or autologous serum is not mixed (NPL 4 to 6).

However, FBS or autologous serum is biologics. There are many problems, such as infection, allergies, operability, and ethics for addition of FBS or autologous serum. On the other hand, substances that adequately replace FBS and autologous serum are not currently known.

Meanwhile, cells, especially cells that are currently in an undifferentiated or low differentiated state and have high potentiality to proliferate, and regenerate and form a tissue or organ in the future, can occasionally unnecessarily differentiate during preservation, and can change to exhibit properties different from those of the tissue or organ that is intended to be regenerated and formed using the cells. Maintaining the undifferentiated or low differentiated state by making cell functions dormant and preventing the unnecessary differentiation over the period of preservation of the cells is an important matter in practice of regenerative medicine, but the means have not yet been established, and establishment of a solution is desired.

Meanwhile, alginic acid or alginate has been conventionally used in the fields of, for example, foods, cosmetics, medical devices, and the like. Alginic acid or alginate is used as a thickener, an active ingredient of health foods having the effect of interfering with absorption of cholesterol, and the like in the food field, as a moisturizer in the cosmetic field, and as a constituent component of an adherent cell culture substrate (PTL 1) in the medical device field.

CITATION LIST

Patent Literature

[PTL 1] Japanese Unexamined Patent Application Publication (Translation of PCT Application) No. 2002-536974

Non Patent Literature

[NPL 1] Crapo P M., et al., An overview of tissue and whole organ decellularization processes. Biomaterials 32, 3233-3243 (2011)
[NPL 2] Hayflick L., et al, Subculturing human diploid fibroblast cultures. Edited by Kruse, P. et al., Tissue Culture Methods and Applications. 220-223 Academic Press (New York) (1973)
[NPL 3] Yamato M., et al., Thermo-responsive culture dishes allow the intact harvest of multilayered keratinocyte sheets without dispase by reducing temperature. Tissue Engineering, 7, 473-480 (2001)
[NPL 4] Juan Jose' Dorantes-Aranda et al. Novel application of a fish gill cell line assay to assess ichthyotoxicity of harmful marine microalgae. Harmful Algae, 10, 366-373 (2011)
[NPL 5] Liang C., et al. Serotonin promotes the proliferation of serum-deprived deprived hepatocellular carcinoma cells via upregulation of FOXO3a. Molecular Cancer 12 (2013) (open access)
[NPL 6] Julia C. et al. Towards a xeno-free and fully chemically defined cryopreservation medium for maintaining viability, recovery, and antigen-specific functionality of PBMC during long-term storage. J. Immunol. Methods 382, 24-31 (2012)

SUMMARY OF THE INVENTION

As described above, in performing a treatment of detaching and suspending cells in tissue or cultured cells, for example, from an organ or tissues of a living body or from a culture substrate of live cells, it is required to (a) prevent death of the cells, and to (b) obtain suspended cells in a state that viability of the cells is maintained, or not to reduce the viability of the cells in detachment and suspension.

Also, in preservation and transportation of cells, it is necessary to protect the cells to prevent death of the cells without reducing the viability of the cells being preserved and transported, in order to let the cells being preserved and transported satisfactorily exert their functions.

Also, it is necessary to maintain cells, especially cells that are currently in an undifferentiated or low differentiated state and have the ability to proliferate and regenerate and form a tissue or organ in the future, in the undifferentiated or low differentiated state by making cell functions dormant and preventing the unnecessary differentiation over the period of preservation of cells.

Also, when suspended cells in a dormant state are adhered to a living organ, a culture substrate, or the like, it is desired that the cells can be easily adhered, and it is necessary to activate and proliferate the adhered cells.

However, in order for the detached and suspended cells to adhere to a scaffold that is a culture substrate such as a wall of a culture vessel or a predetermined carrier, for example, or in order to "plant" such cells, it is necessary to maintain the state of standing still in contact with the scaffold for 12 to 24 hours in an apparatus in which normal culture conditions are kept. If the contact is poor, the cells cannot be planted on the scaffold. In particular, in order to plant cells in specific local sites of a living body, it is necessary to keep the cells in contact with the scaffold of the living body for 12 to 24 hours.

For this purpose, typically, a scaffold such as a nonwoven fabric is brought into contact with cells for 12 to 24 hours outside the living body to adhere the cells to the nonwoven scaffold, and the cells together with the scaffold to which the cells adhere are planted in a desired location in the living body. However, such planting disadvantageously requires time and labor.

In light of the above, it is an object of the present invention to provide a technique enabling safe and easy performance of, for example, a detaching and suspending treatment, a treatment of making cells dormant (dormancy increases the protective effect, and also prevents unnecessary differentiation of cells and maintains an undifferentiated or low differentiated state), a protection treatment for preservation and transportation, and the like while preventing death of cells and maintaining viability of cells in tissue or cultured cells, for example, in an organ or tissue of a living body or in a cell container including a cell culture substrate, and a technique enabling safe and easy performance of an activating treatment of suspended or dormant cells for planting cells in a dormant state (for example, suspended cells).

The present inventor intensively studied to solve the above-described problems. As a result, the inventor found that the above-described problems can be solved by using alginate sulfate. The present invention is summarized as follows.

(1) A cell treatment agent containing alginate sulfate as an active ingredient.
(2) The cell treatment agent according to the above (1), wherein in the alginate sulfate, an alginate sulfate with a sulfate group introduced into a carbon atom at position 6 occupies more than 10% of a total of the alginate sulfate.
(3) The cell treatment agent according to the above (1) or (2) containing at least one selected from the group consisting of a cell culture solution, an extracellular fluid replacement solution, and a maintenance infusion.
(4) The cell treatment agent according to any of the above (1) to (3), for use in cell detachment and suspension of detaching and suspending a cultured cell from a scaffold of a living tissue or from a scaffold of a culture substrate, or detaching and suspending a cell in tissue of a living tissue from a scaffold of the living tissue.
(5) The cell treatment agent according to any of the above (1) to (3), for making a cell in tissue or a cultured cell dormant.
(6) The cell treatment agent according to any of the above (1) to (3), for cell protection of maintaining viability of a cell in tissue or a cultured cell to prevent death.
(7) The cell treatment agent according to any of the above (1) to (3), for cell preservation for maintaining a cell in an undifferentiated state or a low differentiated state.
(8) The cell treatment agent according to any of the above (1) to (3), and (5) to (7), wherein the cell treatment agent is a liquid for cell preservation, tissue preservation, or organ preservation.
(9) A set reagent for activation of a suspended cell or a dormant cell, the set reagent being a combination reagent of the cell treatment agent according to any of the above (1) to (8) and an activator containing a polyvalent cation.

Here, "alginate sulfate" includes pharmaceutically acceptable salts thereof.

The term "scaffold" means what is known as one of the three elements of regenerative medicine in the present technical field.

Adherent cells, which comprise a majority of cells that make up a living body, need to be in a state that the cells are adhered to a fixed base in order to perform their intrinsic functions (including proliferation). This base is called "scaffold" in regenerative medicine. Adherent cells cannot perform their intrinsic functions in the state that they are suspended in liquid. The scaffold can be an artificial scaffold or a scaffold in a natural state. Examples of the artificial scaffold include a wall of a laboratory dish and the like in an artificial substrate for cell culture such as a laboratory dish. Also, fibers that carry cells correspond to the artificial scaffold in the case of planting external cells into a body in a form that the cells are carried and adhered to artificial fibers or the like.

A tissue or an organ of a living body (hereinafter also referred to as "living tissue") is composed of cells and an extracellular matrix (including collagen fibers, proteoglycans, and the like) that surrounds the cells. Adherent cells exist adhering to the extracellular matrix and exert their functions in the living body. Examples of the scaffold in its natural state include extracellular matrix to which cells adhere in a living tissue.

Here, the three elements of regenerative medicine refer to "cells" that constitute a tissue or organ, "bioactive substances" that are signal factors for the function of cells, and "scaffolds" for enabling cells and bioactive substances to move.

"Dormancy" means that cells stop or decrease the activity of proliferation, respiration, metabolism, and differentiation state maintenance while having viability (stopping differentiation state maintenance also means maintaining a dedifferentiation state, namely a low differentiated or undifferentiated state), or means that cells stop or decrease the adhesion.

"Protection" for cells means maintaining viability, namely, preventing the loss of the ability to perform cellular functions and preventing death of cells.

Activation of suspended cells means starting the proliferation, respiration, metabolism, and differentiation state maintenance of the suspended cells in the above-described "dormant" state or in the above-described "protected" state, or restoring the adhesion, respiration, metabolism, and differentiation state maintenance of the suspended cells in the above-described "dormant" state or in the above-described "protected" state. Activation of dormant cells means restarting the proliferation, respiration, metabolism, and differentiation state maintenance of the cells in the above-described "dormant" state or in the above-described "protected" state, or restoring the adhesion, respiration, metabolism, and differentiation state maintenance of the cells in the above-described "dormant" state or in the above-described "protected" state for dormant cells including unsuspended cells, and is synonymous to the later-described "awakening".

The viability means that the cell retains the ability to perform its intrinsic functions (including proliferation function, respiration, metabolism, and differentiation state maintenance) in the living body, in addition to a fact that the cell is alive without dying.

According to the present invention, it is possible to provide a technique enabling safe and easy performance of, for example, a detaching and suspending treatment, a treatment of making cells dormant, a protection treatment for preservation and transportation, and the like while preventing death of cells and maintaining viability of cells in tissue or cultured cells, for example, in an organ or tissue of a living body or in a cell container including a cell culture substrate, and a technique enabling safe and easy performance of an activating treatment of suspended or dormant cells for planting cells in a dormant state (for example, suspended cells).

DESCRIPTION OF EMBODIMENTS

Figure 1:
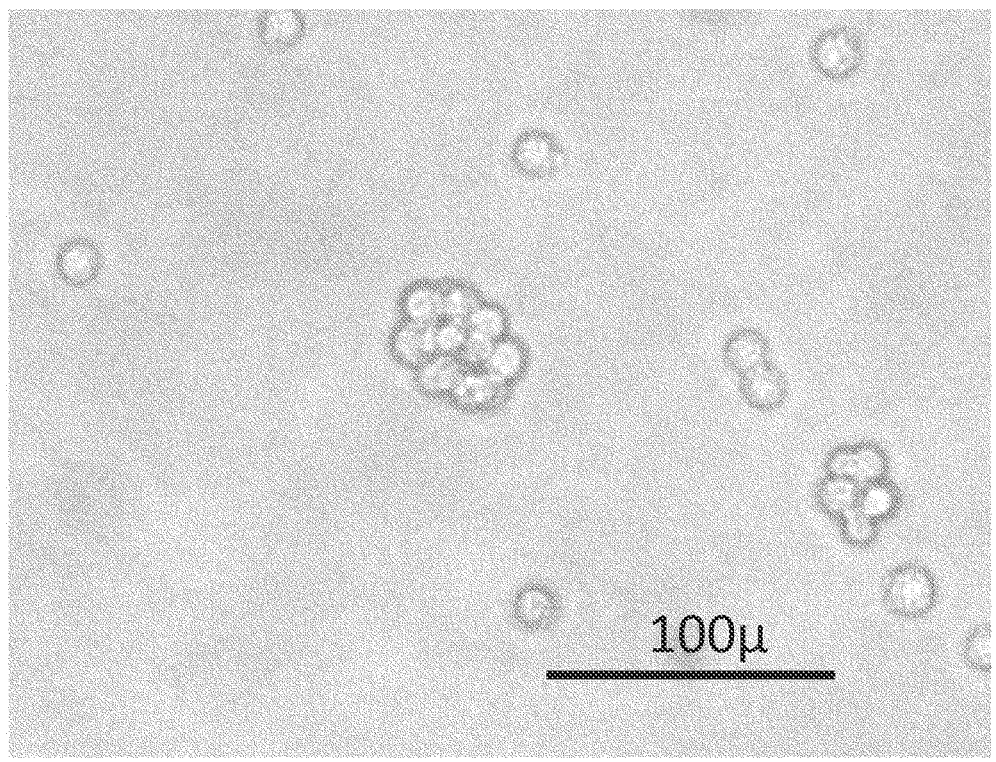
FIG. 1 shows a micrograph image of cells after culturing for 5 days in a cell culture solution containing alginate sulfate in a cell culture incubator ($CO_2$ incubator) under normal culture conditions, namely at 37° C., a carbon dioxide gas concentration of 5%, and a humidity of 100% in Experimental Example 2-2-1.

A cell treatment agent according to an embodiment of the present invention contains alginate sulfate as an active ingredient.

Alginate sulfate is a compound in which a sulfate group is introduced into alginic acid. The alginic acid is a linear polysaccharide composed of two types of monosaccharides, i.e. β-D-mannuronic acid and α-L-guluronic acid, which are found in various brown algae such as kelp and wakame throughout the world. The structure has a portion configured by an M block made up of 1,4 bonded β-(1-4)-D-mannuronic acid, a G block made up of 1,4 bonded α-(1-4)-L-guluronic acid, and an MG block in which mannuronic acid and guluronic acid are alternately 1, 4 bonded. An M/G ratio of alginic acid is known to affect crosslinking reactions (gelation) with divalent metal ions. More specifically, it is known that G-blocks are involved in gelation. This is also applicable to alginate sulfate. Therefore, for gelation of alginate sulfate as will be described later, it is preferred to use the one having such a ratio of G that gives a gel of a desired hardness. Such adjustment of the hardness of the gel can be performed by a conventionally known method. For example, since the content of M or G is specifically different depending on the type and the part of seaweed, alginic acids having different M/G ratios can be obtained by selecting and using appropriate seaweed. Introduction of a sulfate group into alginic acid can also be performed by a conventionally known method. It is also known that alginic acid becomes a smooth sticky aqueous solution (colloidal solution) when dissolved in water, the viscosity (viscosity) of this aqueous solution is proportional to the polymerization degree of the alginic acid, and the viscosity of the aqueous solution increases as the polymerization degree increases. This point is also applicable to alginate sulfate. Such alginic acids having different viscosity types are commercially available, and various types including those forming a general sticky aqueous solution, and those referred to as a low viscosity type (for example, KIMICA ALGIN ULV series, available from KIMICA Corporation, etc.) having a viscosity adjusted to be lower than that of a general one, can be used.

A pharmaceutically acceptable salt of alginate sulfate is such that hydrogen ions of the carboxylic group and the sulfonic group of the alginate sulfate are liberated and bond to cations. Such cations may be those capable of forming pharmaceutically acceptable salts, and examples of the cations include monovalent cations such as sodium ions, potassium ions, and ammonium ions.

The position of introduction of a sulfate group in alginate sulfate is preferably the carbon atom at position 6 from the viewpoint of high treatment capacities for cells. It is preferred that the introduction amount is more than 10% in the entire alginate sulfate. The treatment capacities tend to increase as the introduction amount increases, such as 20% or more, 30% or more. 40% or more, 50% or more, 60% or more, 70% or more, and 80% or more. The number of sulfate groups introduced per one monosaccharide molecule, that is, the degree of substitution (DS), is not particularly limited, but when the remaining conditions are the same, the treatment capacities tend to increase as the DS increases. Since the treatment capacities may be adjusted according to the application target, the content of the treatment, and the like, the adding amount of alginate sulfate can be increased by decreasing the DS, or the adding amount of alginate sulfate can be decreased by increasing the DS according to the situation. According to confirmation by the inventor, for example, the detection limit when the DS was measured by the later-described method was 0.00001. Also, the inventor confirmed that even when alginate sulfate having a DS of 0.00001 is used, excellent treatment capacities can be exerted by adjusting the concentration of alginate sulfate to be added. Therefore, when it is necessary to ensure the treatment capacities while keeping the alginate sulfate concentration in the application target somewhat low, the DS is, for example, preferably 0.5 or more, more preferably 0.7 or more, and further preferably 0.9 or more. When the alginate sulfate concentration in the application target may be somewhat high, the DS can be, for example, 0.00001 or more, under a condition that the desired treatment capacities are exerted.

A dosage form of the cell treatment agent is not particularly limited, and can be appropriately determined as powder, liquid, or the like using an appropriate excipient according to various applications. Also, if necessary, various additives can be added.

For example, when desired cells are cultured in a general cell culture solution and then the cells are administered into a body, the cells are separated from the cell culture solution, and washed to remove various reagents, not used for medical purposes, contained in the cell culture solution, and then the obtained cells are immersed in an extracellular fluid replacement solution, a maintenance infusion, or the like, and can be administered to the body. The extracellular fluid replacement solution is a group of liquids having an electrolyte composition similar to the extracellular fluid surrounding cells in a living body, and the maintenance infusion is an infusion solution that is administered while nutrients such as sugars, proteins (amino acids), and fats and micronutrients are added to the daily water content and the electrolyte required for humans to maintain life. The extracellular fluid replacement solution and the maintenance infusion are medical liquids used as solvents for injection solutions of other active ingredients or for intravenous drip injection of the same alone, and the safety of administration into bodies has been established. Thus, for the electrolyte composition similar to the environment surrounding cells and safety, an extracellular fluid replacement solution or a maintenance infusion is suitable as an excipient of a cell treatment agent used in administering cells into a body in regenerative medicine, Examples of the extracellular fluid replacement solution include so-called replacement infusions used for the purpose of replenishing the loss of extracellular fluid, and more specific examples include a Ringer's solution, a lactated Ringer's solution, an acetated Ringer's solution, a bicarbonate Ringer's solution, a Hartmann solution, saline, a plasma substitute, a plasma preparation, and the like. Among these, for example, replacement infusions that are not derived from human such as a plasma substitute or a plasma preparation are desirable. Examples of the maintenance infusion include: a sugar and electrolyte infusion preparation that does not contain amino acid; a sugar, electrolyte and amino acid infusion preparation; a sugar, electrolyte, amino acid, and multivitamin liquid preparation; a sugar, electrolyte, amino acid, multivitamin, and trace element liquid preparation; and a sugar, electrolyte, amino acid, and fat emulsion, and the like.

Meanwhile, when cells are separated from a general cell culture solution and washed, and then immersed in a so-called extracellular fluid replacement solution to prepare a cell treatment agent as described above, these operations may reduce the viability of cells or cause infection. Meanwhile, the present inventor has found that alginate sulfate has a cell protective effect in the extracellular fluid replacement solution as well as in a general cell culture solution. That is, an extracellular fluid replacement solution, a maintenance infusion, or the like containing alginate sulfate, can be used as a substitute for a cell culture solution, for example, in storage and transportation, and in administration, the cells can be immediately administered while they are immersed in the extracellular fluid replacement solution. Therefore, it is possible to prevent the decrease in viability and the risk of infection caused by transferring cells from the culture solution to a so-called extracellular fluid replacement solution, maintenance infusion, or the like.

The above-described cell treatment agent can be used as a reagent in a predetermined dosage form containing alginate sulfate as an active ingredient. Therefore, by adding or applying the reagent to a culture substrate such as a culture solution, a culture vessel, or a carrier of a cell, or to a living tissue such as an organ of a living body, it is possible to (a) detach cultured cells grown on a scaffold of the culture substrate or on a scaffold of the living tissue from the scaffold of the culture substrate or the scaffold of the living tissue and suspend the same, and to (b) detach cells in tissue of the living tissue from the scaffold (living organ, etc.) of the living tissue and suspend the same. Therefore, the cell treatment agent can be suitably used for cell detachment and suspension.

The above-described cell treatment agent can stop proliferation, stop adhesion, or maintain an undifferentiated or low differentiated state without allowing differentiation of the cells while maintaining the viability of the cells, in other words, can make cells dormant, for cells in tissue of a biological tissue, or cultured cells on the scaffold of the culture substrate or on the scaffold of the living tissue. Therefore, the cell treatment agent can be suitably used for cell dormancy for making these cells dormant. Owing to this dormancy effect, cells stop proliferating, but are in such a state that they awaken and re-adhere to the culture substrate or the living tissue and start proliferation when the conditions are satisfied. Thus, the cell treatment agent is effective in the point of being capable of temporarily making cells dormant, stopping activities of the cells for preserving and transporting the cells, and resuming the activities at desired timing, and in the point of capable of directly making suspended cells obtained by a detachment and suspension treatment dormant. In addition, since the above-described cell treatment agent is capable of maintaining cells in an undifferentiated or low differentiated state, it is also suited for cell preservation that enables a tissue or an organ exhibiting desired properties to be regenerated or formed after awakening of the cells from the dormant state.

The above-described cell treatment agent has a cell protective effect of maintaining viability of cells in tissue or cultured cells in a cell container including a culture vessel or a storage vessel, or in a biological tissue to prevent death of the cells. Therefore, the cell treatment agent can be used as a substitute for FBS or human serum, which has been conventionally used for having the protective effect of preventing cell death. Therefore, it is possible to safely prevent cell death and protect cells without using FBS or human serum. The cell treatment agent having the cell protective effect is suitable, for example, for preserving and transporting cells. In particular, as described above, the cell treatment agent containing an extracellular fluid replacement solution or a maintenance infusion solution as an excipient, and alginate sulfate as an active ingredient can protect cells even during preservation and transportation, and can be administered directly as it is. Therefore, the cell treatment agent greatly contributes to the safety and convenience of medical care.

Since the cell treatment agent can function, for example, for cell dormancy, for cell protection, or for cell preservation for maintaining cells in an undifferentiated or low differentiated state as described above, the cell treatment agent in a liquid dosage form is suitable as a liquid for the preservation of cells, tissues, or organs. In this case, the dosage form is preferably a cell culture solution, an extracellular fluid replacement solution, a maintenance infusion, or the like. The cell culture solution applicable to various applications is not particularly limited, and a general serum-free cell culture solution, a general FBS-added cell culture solution, or the like can be selected and adopted according to the application and the like.

Alginate sulfate, which is the active ingredient of the above-described cell treatment agent, exhibits the effect of detaching and suspending cells while exhibiting the effect of making cells dormant. However, the inventor found that coexistence of alginate sulfate and an activator containing polyvalent cations causes activation of suspended cells and non-suspended dormant cells, for example, activation of the adhesivity of suspended cells and awakening from the dormant state of dormant cells (for example, proliferability, etc.). Polyvalent cations contained in the activator serve as a crosslinking agent and bind to alginate sulfate, and can form a hydrophilic and nonliquid gel just like an extracellular matrix. Therefore, for example, when an activator containing polyvalent cations is added to a culture solution or the like of cells suspended in a liquid such as a culture solution containing alginate sulfate, it is possible to activate the adhesivity of the suspended cells by the polyvalent cations such as divalent metal ions, and at the same time, it is possible to easily form such a state that cells are adhered to a scaffold of alginate sulfate gelated by crosslinking with the polyvalent cations. Furthermore, since dormant cells in a dormant state are awakened by polyvalent cations, cells being in a dormant state (for example, a proliferation stopped state that is one phenomenon of dormancy) due to the action of alginate sulfate awaken and can start re-adhesion and re-proliferation when the cells are cultured under predetermined conditions. Thus, use of the above-described cell treatment agent containing alginate sulfate in combination with an activator containing polyvalent cations enables cell detachment, suspension, and introduction into a dormant state, and inversely enables activation of not only suspended cells but also adhered cells in a dormant state. Although the interrelation between the cell adhesivity activating effect of polyvalent cations and the awakening effect of dormant cells, and the gelation of alginate sulfate has not been recognized well, the combination of alginate sulfate and polyvalent cations is suited as a set reagent for controlling cell detachment, suspension, and introduction into a dormant state, and inverse effects including adhesion of cells and awakening of dormant cells.

Here, the adhesivity of suspended cells is an inverse phenomenon to the above-described detachment and suspension of cells, and means that the cells change from the isolated cell state to the clustered cell group or the cells adhered to the scaffold, or from the clustered cells to the cells adhered to the scaffold. The ability of cells to cause the adhesion is called adhesivity of cells, and transition from the adhesivity decreased state to the adhesivity restored state is rephrased as activation of the adhesivity. Whether the adhesivity of suspended cells has been activated can be evaluated, for example, by counting the number of adhered cells after leaving the culture solution containing the suspended cells to stand for a period of time that allows the cells to sufficiently adhere to the scaffold, and comparing with the control. The ability to cause cell division and increase the number of cells is called proliferability of cells, and transition from the proliferability decreased or stopped state in the dormant state to the proliferability restored state is rephrased as activation of the proliferability. Whether the proliferability of dormant cells has been activated can be evaluated, for example, by counting the number of cells after culturing the culture solution containing the dormant cells under predetermined conditions, and comparing with the control.

Alginate sulfate exhibits the effect of detaching and suspending adhered cells from the scaffold, and at the same time, the detached and suspended cells tend to become dormant. However, depending on the type of cell and various conditions, cells can be in a dormant state although the cells are not detached and suspended. That is, the adhered cells can be in a dormant state. Coexistence of the activator with alginate sulfate makes it possible to activate cells that have been temporarily dormant by alginate sulfate regardless of whether or not the cells are suspended.

While the activator is not particularly limited as long as it contains polyvalent cations and is capable of activating suspended cells or dormant cells, and is safely applicable to a living body or the like, those capable of gelating alginate sulfate are preferred from the viewpoint of further promoting the activation of suspended cells or dormant cells. Examples of such activators include: aqueous solutions containing polycations such as chitosan, or polyvalent cations such as aluminum ions, iron ions, magnesium ions, or calcium ions; chelated preparations of polyvalent cations; solids that generate insoluble polyvalent cations such as powder of aluminum compounds, iron compounds, magnesium compounds, or calcium compounds; and cloth pieces in which these polyvalent cation suppliers are impregnated or carried on a surface. Examples of the calcium ion source include water-soluble calcium chloride and water-insoluble calcium phosphate. Examples of the calcium ion supplier include chelated calcium and the like. Examples of the fabric include gauze, made of biocompatible fibers, that is applicable to a living body.

The adding amount in various applications can be appropriately determined according to the application target, the composition of alginate sulfate, and the like. For example, when alginate sulfate having a DS of 0.9 is applied to a culture solution, the above-described various effects tend to be easily exerted when the concentration of the alginate sulfate in the culture solution is preferably 0.001 to 50 mg/ml, more preferably 0.05 to 40 mg/ml, and further preferably 0.1 to 20 mg/ml. For example, in the application for the dormancy effect, the concentration is preferably 0.001 mg/ml or more, and more preferably 0.00625 mg/ml or more. In the application for the cell detaching and suspending effect, the concentration is preferably 0.01 to 50 mg/ml. In the application for the cell protective effect, the concentration is preferably 0.0001 to 10 mg/ml.

The cell treatment agent and the set reagent described above are applicable to various cells and are suitable for live cells derived from, for example, plants, humans, and animals other than humans.

EXAMPLES

Hereinafter, embodiments of the present invention will be described in detail on the basis of examples. In the examples shown below, various effects on cells in a cell culture vessel or storage vessel are verified, however, it goes without saying that the same effects are also exhibited on cells in living tissues or spheroid cells.

Production Example 1: Production of Alginate Sulfate A

Alginate sulfate (alginate sulfate A) in which a sulfate group is randomly introduced into alginic acid was prepared in accordance with the method described in the publicly known literature "Whistler R L, et al., Sulfates. Edited by Whistle R L., et al., Methods in Carbohydrate Chemistry. Vol. II, 298-303. Academic Press (New York) (1963)". That is, after stirring sodium alginate (available from Fujifilm Wako Pure Chemical Co., Ltd., guaranteed reagent) and a sulfur trioxide pyridine complex in dimethylformamide (40° C., 12 hours) to introduce a sulfate group into alginic acid, alginate sulfate was precipitated, and neutralized and dissolved in a dilute sodium hydroxide aqueous solution, and then dialyzed for 72 hours and lyophilized to prepare alginate sulfate A. The alginate sulfate A was dissolved in purified distilled water or the like and adjusted to have a predetermined concentration before use. The obtained alginate sulfate A was confirmed to have a sufficient quantity of sulfate groups with a degree of substitution (DS), per monosaccharide molecule, of 0.9 in the later-described physical property evaluation.

Production Example 1-2: Production of Alginate Sulfate A-2

Alginate sulfate A-2 with a predetermined degree of substitution was obtained in the same manner as in Production Example 1 except that the reaction temperature and time were adjusted to achieve the later-described degree of substitution and sodium alginate and a sulfur trioxide pyridine complex were stirred in dimethylformamide. Alginate sulfate. A-2 was confirmed to have a DS of 0.001 in the physical property evaluation described later.

Production Example 1-3: Production of Alginate Sulfate A-3

Alginate sulfate A-3 with a predetermined degree of substitution was obtained in the same manner as in Production Example 1 except that the reaction temperature and time were adjusted to achieve the later-described degree of substitution and sodium alginate and a sulfur trioxide pyridine complex were stirred in dimethylformamide. Alginate sulfate A-3 was confirmed to have a DS of 0.0001 in the physical property evaluation described later.

Production Example 1-4: Production of Alginate Sulfate A-4

Alginate sulfate A-4 with a predetermined degree of substitution was obtained in the same manner as in Production Example 1 except that the reaction temperature and time were adjusted to achieve the later-described degree of substitution and sodium alginate and a sulfur trioxide pyridine complex were stirred in dimethylformamide. Alginate sulfate A-4 was confirmed to have a DS of 0.00001 which is a quantitative measurement limit in the physical property evaluation described later.

Production Example 1-5: Production of Alginate Sulfate A-5

Low-viscosity type alginate sulfate A-5 with a predetermined degree of substitution was obtained in the same manner as in Production Example 1-2 except that a low-viscosity type (low molecular weight type) sodium alginate (available from Kyosei Pharmaceutical Co., Ltd.) was used in place of sodium alginate (available from Fujifilm Wako Pure Chemical Co., Ltd., guaranteed reagent). Alginate sulfate A-5 was confirmed to have a DS of 0.001 in the physical property evaluation described later. The viscosity of alginate sulfate A-5, measured by a viscometer at an environmental temperature of 20° C. using a 10% aqueous solution, was 26 mPa·s.

Production Example 1-6: Production of Alginate Sulfate A-6

Alginate sulfate A-6 with a predetermined degree of substitution was obtained in the same manner as in Production Example 1 except that sodium alginate 80-120 (available from Fujifilm Wako Pure Chemical Co., Ltd., extra pure reagent) was used in place of sodium alginate (available from Fujifilm Wako Pure Chemical Co., Ltd., guaranteed reagent) and the reaction temperature and time were adjusted to achieve the later-described degree of substitution. Alginate sulfate A-6 was confirmed to have a DS of 0.25 which is a quantitative measurement limit in the physical property evaluation described later.

Production Example 2: Production of Alginate Sulfate B

Alginate sulfate (alginate sulfate B) in which a sulfate group is preferentially introduced into the carbon atom at position 6 of alginic acid was prepared in accordance with the method described in the publicly known literature "Hoiberg C P., et al., Preparation of sulfate esters. Reactions of various alcohols, phenols, amines, mercaptans, and oximes with sulfuric acid and dicyclohexylcarbodiimide J. Am. Chem. Soc. 91. 4273-4278 (1969)". That is, first, the alginate was made into an H form by an ion exchange resin column, and then neutralized with pyridine to a form of a pyridinium salt for easy dissolution in a solvent. This was then dissolved in N,N-dimethylformamide to cause dehydration condensation reaction with sulfuric acid at 0° C. for 60 minutes using dicyclohexylcarbodiimide to introduce a sulfate group to the carbon atom at position 6. The obtained alginate sulfate (hereinafter, also referred to as "6-sulfate group alginic acid") was confirmed to have a sufficient quantity of sulfate groups with a degree of substitution (DS), per monosaccharide molecule, of 0.9. Also, the carbon atom into which the sulfate group was introduced was examined by the method described later for the obtained alginate sulfate B, and it was confirmed that introduction into the carbon atom at position 6 occupied 80% or more and introduction at the position 2 occupied 20% or less.

Production Example 3: Production of Alginate Sulfate C

Alginate sulfate (alginate sulfate C) in which a sulfate group is introduced to a site other than the carbon atom at position 6 was prepared in accordance with the method described in the publicly known literature "Matsuo M., et al., A novel regioselective desulfation of polysaccharide sulfates: specific 6-O-desulfation with N,O-bis(trimethylsilyl)acetamide Carbohydr. Res., 241, 209-215 (1993)". In the method, alginate sulfate C is obtained by removing the sulfate group introduced into the carbon atom at position 6 using alginate sulfate A, having a degree of substitution of 1.7 or more per monosaccharide molecule, out of alginate sulfates A obtained in Production Example 1. More specifically, a pyridinium salt of alginate sulfate A obtained in Production Example 1 and the N-methyl-N-trimethylsilyl-trifluoroacetamide were heated in pyridine to specifically remove the sulfate group introduced into the carbon atom at position 6 to obtain alginate sulfate C. The obtained alginate sulfate C had a sufficient amount of sulfate groups with a degree of substitution (DS), per monosaccharide molecule, of 0.9. Also, the carbon atom into which the sulfate group was introduced was examined by the method described later, and it was confirmed that introduction of a sulfate group into the carbon atom at position 6 occupied 10% or less.
(Evaluation)
<Determination of Number of Substituted Sulfate Groups>
In accordance with the method of Kasai et al. (Yutaka. KASAI et al., "Preparation and electrochemical properties of alginate sulfate electrolyte membranes", KOBUNSHI RONBUNSYU, 65, 4, 295-300 (2008)), the quantity of substituted sulfate groups in alginate sulfate was measured. That is, a sulfur content was measured using an X-ray analyzer. Also, Fourier transform infrared spectroscopic measurement was performed by the ATR method, and the presence/absence of a new absorption peak based on S=O stretching vibration and S—O stretching vibration was examined. The degree of substitution of sulfate group was expressed by the number of sulfate groups per one monosaccharide molecule (average value), that is, by the degree of substitution (DS).

<Position of Sulfate Group-Introduced Carbon Atom and Ratio of Introduction of Sulfate Group>
The position of the carbon atom into which a sulfate group was introduced, and the ratio of sulfate groups in alginate sulfate were determined in accordance with the method described in the publicly known literatures "Yoshida T., et al., Synthesis and structural analysis of curdlan sulfate with a potent inhibitory effect of AIDS virus infection. Macromolecules 23, 3717-3722 (1990)" and "Yamagaki T., et al., NMR Spectroscopic Analysis of Sulfated β-1,3-Xylan and Sulfation Stereochemistry. Biosci. Biotech, Biochem., 61 (8), 1281-1285 (1997)". That is, using 13-C NMR and two-dimensional NMR, the position and the ratio of introduction of sulfate groups were determined according to the findings that the carbon atom portion into which a sulfate group was introduced shifted to a low magnetic field, and an H—H COSY spectrum, a C—H COSY spectrum, and the like.

Table 1 shows the above-described evaluation results of alginate sulfates obtained in Production Examples 1 to 3.

TABLE 1

| | Degree of substitution (DS) of sulfate group per one molecule of monosaccharide | Position and ratio of sulfate group introduction |
|---|---|---|
| Alginate sulfate A | 0.9 | Non-specific |
| Alginate sulfate A-2 | 0.001 | Non-specific |
| Alginate sulfate A-3 | 0.0001 | Non-specific |
| Alginate sulfate A-4 | 0.00001 | Non-specific |
| Alginate sulfate A-5 | 0.001 | Non-specific |
| Alginate sulfate A-6 | 0.25 | Non-specific |
| Alginate sulfate B | 0.9 | 80% or more in carbon atoms at position 6 20% or less in carbon atoms at position 2 |
| Alginate sulfate C | 0.9 | Sulfate groups in carbon atoms at position 6 were 10% or less |

Experimental Example 1 Cell Detaching and Suspending Effect

Experiments were conducted using Chinese hamster fibroblasts as mesenchymal cells and rat corneal epithelial cells as epithelial cells. A serum-free cell culture solution to which FBS or the like was added at a concentration of 10% (hereinafter also referred to as "normal FBS-added cell culture solution") was prepared, and the aforementioned fibroblasts or corneal epithelial cells were added thereto at a concentration of $10^6$ cells/ml, and cultured for 24 hours under normal cell culture conditions (37° C., humidity 100%, carbon dioxide gas concentration 5%), and the cultured cells were sufficiently adhered to the wall of the culture dish. Thereafter, the cell culture solution in the culture dish was replaced with aqueous solutions of alginate sulfates A to C obtained in Production Examples 1 to 3 and having concentrations of 0.01, 0.1, 1, 10, and 50 mg/ml, and cell culture was continued under normal conditions. As comparative controls, samples replaced with aqueous solutions of non-sulfated normal alginic acid of the same concentrations were used. For these samples, cell detachment and suspension were observed over time. The point of time at which 90% or more of the cells have been detached and suspended is determined as "cell detachment and suspension". Table 2 shows the results (average values) of rat corneal epithelial cells for the case of N=4. In Table 2, a sample in which cells were detached and suspended is marked with "o", and a sample in which cells were not detached and suspended is marked with "x".

TABLE 2

| Concentration (mg/ml) of alginate sulfate or alginic acid in replacement liquid | Lapse time (hour) after replacement with replacement liquid | | | | | |
|---|---|---|---|---|---|---|
| | 3 | 6 | 12 | 18 | 24 | 48 |
| Alginate sulfate A  0.01 | | | x | | | o |
| 0.1 | | x | | | o | |
| 1 | | x | | | o | |
| 10 | x | | | o | | |
| 50 | x | | | | o | |
| Alginate sulfate B  0.01 | | | x | | | o |
| 0.1 | | x | | | | o |
| 1 | | x | | | o | |
| 10 | x | | | o | | |
| 50 | x | | | o | | |
| Alginate sulfate C  0.01 | | | x | | | o |
| 0.1 | | x | | | o | |
| 1 | | x | | | o | |
| 10 | x | | | | o | |
| 50 | x | | | o | | |
| Alginic acid  0.01 | | | | | x | |
| (Control)  0.1 | | | | | x | |
| 1 | | | | | x | |
| 10 | | | | | x | |
| 50 | | | | | x | |

As shown in Table 2, any of alginate sulfates A to C detached and suspended adhered cells within a predetermined time depending on the concentration. In addition, the sample in which a sulfate group is preferentially introduced into a carbon atom at position 6 as in alginate sulfate B showed higher effect of detaching and suspending cells in comparison with alginate sulfate A in which a sulfate group is randomly introduced, and alginate sulfate C in which a sulfate group is preferentially introduced into a position other than position 6. On the other hand, detachment and suspension were not observed with normal alginic acid.

The same results were observed in experiments using Chinese hamster fibroblasts.

These results reveal that alginate sulfate is suitable as a cell treatment agent for cell detachment and suspension for detaching and suspending cells.

Experimental Example 2. Dormancy Effect on Suspended Cells, and Re-Adhesion and Proliferation After Awakening Experimental Example 2-1

Whether cells detached and suspended using replacement liquids of 1 mg/ml of alginate sulfates A to C in Experimental Example 1 show difference in survival of cells, as compared with a conventional trypsin method, was examined. The trypan blue excretion test, which is an ordinary method of confirming survival of cells, was performed according to a method described in the publicly known literature "Denizot F., et al., Rapid colorimetric assay for cell growth and survival. Modifications to the tetrazolium dye procedure giving improved sensitivity and reliability. J. Immunol. Methods, 89, 271-277 (1986)". The CytoRed-stained viable cell red fluorescent observation method by which viable cells can be observed under a fluorescence microscope in a stereoscopic view was performed according to the method described in the publicly known literature, "Ishiyama M., et al., A resorufin derivative as a fluorogenic indicator for cell viability, Anal. Sci., 15, 1025-1028 (1999)". From these tests, a viable cell rate (number of viable cells total number of cells×100%) of cells detached and suspended by alginate sulfate B was calculated. Also, as a comparative control, a viable cell rate (viability) of cells detached and suspended by the trypsin method was calculated and compared.

The trypsin method was performed in the following manner by an ordinary method without using the aqueous solution of alginate sulfate in Experimental Example 1.

The cell culture solution in the cell culture vessel was sucked out, and the cell surface was washed with about half of the amount for use in culture of PBS (−) (PBS not containing $Ca^{2+}/Mg^{2+}$). Thereafter, 1 mL of 0.2% trypsin/EDTA solution was distributed in the vessel with respect to the cell surface of 25 $cm^2$ to let trypsin act, and then the excess trypsin solution was removed. The culture vessel was incubated in a $CO_2$ incubator for 2 minutes under normal conditions (37° C., carbon dioxide gas concentration 5%, humidity 100%), and cell detachment was examined. Trypsin was then inactivated with a trypsin inhibitor when a serum-free cell culture solution was used. In conducting FBS-added cell culture, an FBS-added cell culture solution was added and trypsin was inactivated. Suspended cells were obtained in the same manner as in Experimental Example 1 except for the forgoing operations. The obtained suspended cells were subjected to a live or dead assay for cell.

Table 3 shows the results of cells that are detached and suspended with a replacement liquid of 1 mg/ml alginate sulfate B, and a comparative control. The cultured cells are rat corneal epithelial cells, and the results are obtained for N=4. The viable cell rate of the cells determined by the trypan blue excretion test and the live or dead assay ranged from 95 to 106% in cells detached and suspended by the trypsin method, when the viable cell rate (average) was 100%. The viable cell rate when detached with alginate sulfate B was 101% on average, and distributed in the range between 95 and 106%, compared with the average of 100% by the trypsin method, and the result was equivalent to that by the trypsin method. This demonstrates that detaching and suspending cells with alginate sulfate is a comparably safe method for cell survival compared to the trypsin method of the conventional method.

TABLE 3

| Cell detaching and suspending method | Average (%) | Range (%) |
|---|---|---|
| Trypsin method | 100 | 95 to 106 |
| Alginate sulfate B | 101 | 95 to 106 |

Experimental Example 2-2

It is known that when cells detached and suspended by the trypsin method are transferred to an FBS-added cell culture solution after trypsin removal and inactivation, and cultured in normal culture conditions (37° C., humidity 100%, carbon dioxide gas concentration 5%), the suspended cells adhere on the inner wall of the culture vessel as a scaffold in 12 hours to 24 hours, and the cells exponentially proliferate by culturing the cells for 5 to 7 days. The cells detached and suspended with alginate sulfate were cultured for a long term of 5 days in an FBS-added cell culture solution containing the same concentration of alginate sulfate, and then the suspended cells were cultured in an FBS-added cell culture solution not containing alginate sulfate. Then, whether the cells adhered to the inner wall of the culture vessel and proliferated comparably to the cells that were detached and suspended by the trypsin method and cultured in an FBS-added cell culture solution after trypsin removal and inactivation, was examined in the following manner. In the following Experimental Examples 2-2-1, 2-2-2, rat corneal epithelial cells were used.

Experimental Example 2-2-1

Cells detached and suspended by alginate sulfate were cultured in advance in an FBS-added cell culture solution containing the same concentration of alginate sulfate for 5 days under normal conditions. For the 5 days, whether the cells were suspended and the number of cells did not increase at all, namely, whether the cells stopped proliferation and were dormant was examined by cell number comparison through microscopic observation and MTT assay method (Gerlier D., et al, Use of MTT colorimetric assay to measure cell activation. J. Immunol. Methods, 94, 57-63, (1986)) which is a standard method for comparison of the number of viable cells.

The examination results are shown in FIG. 1 and Table 4. Table 4 shows the results for N=4 using a cell culture solution having a concentration of 1 mg/ml of alginate sulfate B. It was found that before and after 5 days of normal culture in a cell culture solution containing alginate sulfate, the cells remained unchanged while keeping the state that the cells were suspended and a cluster was formed in the same manner (FIG. 1), and the number of cells did not increase (Table 4). That is, it was confirmed that the suspended cells stop proliferation while having viability and are dormant in a suspended state in the cell culture solution containing alginate sulfate.

TABLE 4

| | Average (%) | Range (%) |
|---|---|---|
| Before 5 days of culture | 100 | 95 to 106 |
| After 5 days of culture | 99 | 93 to 107 |

Experimental Example 2-2-2

Figure 2:
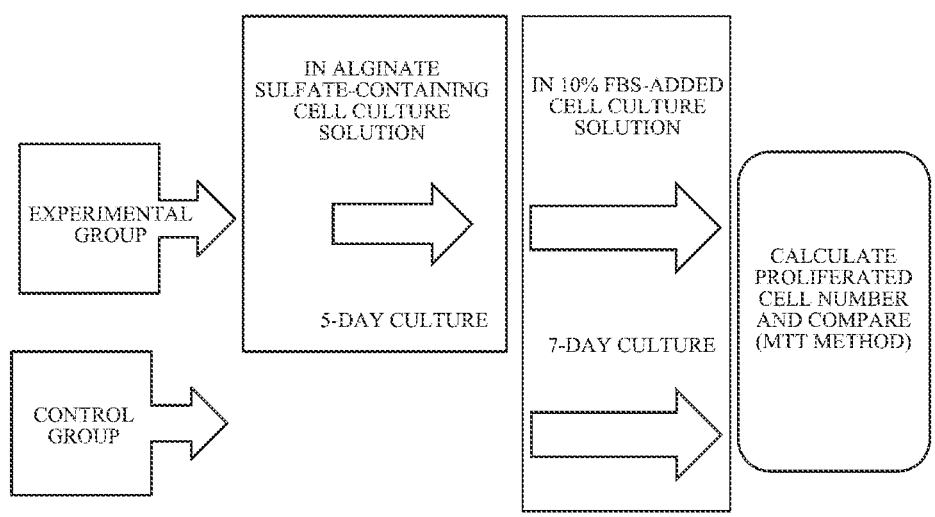
FIG. 2 shows an experimental schema performed in Experimental Example 2-2-2.

Examination was performed according to the experimental schema shown in FIG. 2. As a comparative control group, the same number of cells suspended by the trypsin method (that had not been previously cultured for 5 days) were transferred into a normal FBS-added cell culture solution and cultured under normal conditions for 7 days. The cell culture of the comparative control group was normal cell culture, and within 7 days the cells proliferated and the number of cells increased significantly.

As an experimental group, cells cultured under normal conditions for 5 days in an FBS-added cell culture medium containing alginate sulfate B were then transferred to a normal FBS-added cell culture solution (not containing alginate sulfate), and cultured under normal culture conditions for 7 days. Between the comparative control group and the experimental group, the number of proliferated cells was compared by the MTT assay after the 7 days of culture, and the growth ability was compared between these groups.

The results are shown in Table 5. Both in the experimental group and the comparative control group, culture was started under normal culture conditions in a normal FBS-added cell culture solution, and within 24 hours the cells were adhered to a scaffold of the inner wall of the culture vessel. Then, after culturing under normal culture conditions for 7 days, the number of viable cells in the experimental group was 104% on average (range: 100 to 110%) when the average number of viable cells in the comparative control group was defined as 100%. This indicates that the cells in the experimental group also adhered to the scaffold as with the cells in the comparative control group, and significantly proliferated comparably or better than the case of the comparative control group when the cells were cultured under normal culture conditions.

That is, it was found that suspended cells that are detached and suspended with alginate sulfate re-adhere to the cell culture vessel and proliferate comparably to the cells that are cultured under normal culture conditions immediately after being detached and suspended by the trypsin method (comparative control group) even when the cells are cultured under normal conditions in a state that the cells are suspended in an alginate sulfate-containing cell culture solution for a long term of 5 days (experimental group).

Thus, even when cells are detached and suspended with alginate sulfate, and left to stand in a cell culture solution in the presence of alginate sulfate, it is possible to make cells re-adhere and proliferate comparably to the conventional general treatment. This reveals that detachment and suspension of cells using alginate sulfate is not cytotoxic and can make suspended cells dormant.

TABLE 5

| Cell detaching and suspending method | Average (%) | Range (%) |
|---|---|---|
| Trypsin (Control group) | 100 | 97 to 107 |
| Alginate sulfate B (Experimental group) | 104 | 100 to 110 |

Experiments were conducted in the same manner using alginate sulfates A, C in place of alginate sulfate B, and the same experimental results were observed.

Experimental Example 2-2-3

The concentration of alginate sulfate at which suspended cells re-adhere from the dormant state and proliferate was examined by a method applying the colony formation inhibition test described in ISO 10993-5 (Biological evaluation of medical devices Part 5: Tests for vitro cytotoxicity). The experimental method is as follows. The cells used in the experiment were of the same two types as in Experimental Example 1.

The culture solution of the laboratory dish containing cells adhered to the laboratory dish in the FBS-added cell culture solution was replaced by an FBS-added cell culture solution containing alginate sulfate B at a starting concentration of 10 to 0.1 mg/ml to temporarily suspend the cells. Then, a normal (namely, not containing alginate sulfate) FBS-added cell culture solution was added to the cell culture solution (starting concentration of alginate sulfate of 10 to 0.1 mg/ml) to adjust the concentration of alginate sulfate into conditions respectively having alginate sulfate concentrations diluted stepwise from 1-fold dilution (namely, undiluted, equal to dilution degree 100%, the concentration of alginate sulfate is 10 to 0.1 mg/ml, equivalent to the starting concentration) to 100-fold dilution (namely, dilution degree 1%, the concentration of alginate sulfate is 0.1 to 0.001 mg/ml, which is 1% of the starting concentration). In cell culture solutions adjusted to the conditions, cells were cultured under normal culture conditions (37° C., humidity 100%, carbon dioxide gas concentration 5%) for 7 days.

For these cells (experimental group), whether or not cell re-adhesion and cell proliferation occurred as usual in the same manner as in later-described Comparative control 1 and Comparative control 2 was observed. The degree of cell proliferation was examined by determining the number of colonies formed after 7 days, and comparing by a method conforming to the above-described colony formation inhibition test.

As Comparative control 1, the culture solution of the laboratory dish containing cells adhered to the laboratory dish in the FBS-added cell culture solution was replaced by an FBS-added cell culture solution containing 10 to 0.1 mg/ml alginate sulfate B to temporarily suspend the cells, and then the resultant cell culture solution was replaced by a normal (namely, not containing alginate sulfate) FBS-added cell culture solution. Then, the same operation as the stepwise dilution in the experimental group was conducted by further adding a normal FBS-added cell culture solution. Following this operation, cells were cultured under normal culture conditions (37° C., humidity 100%, carbon dioxide gas concentration 5%) for 7 days.

As Comparative control 2, cells suspended by the ordinary trypsin method were used. These cells were transferred to a normal FBS-added cell culture solution, and cultured under normal culture conditions (37° C. humidity 100%, carbon dioxide gas concentration 5%) for 7 days. For Comparative controls 1, 2, it was confirmed that cell re-adhesion and cell proliferation occurred as usual. The cell proliferation was examined by calculating the number of colonies formed after 7 days, and comparing by a method conforming to the above-described colony formation inhibition test. Thus, Comparative control 2 was used as a standard for a colony formation rate of 100%.

Figure 3:
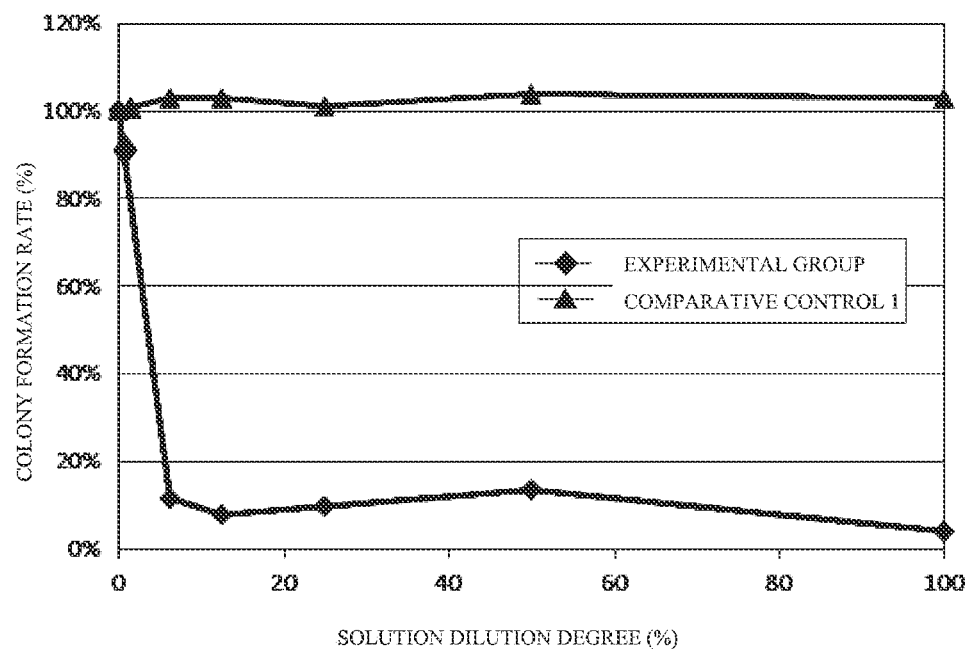
FIG. 3 shows results of a colony formation inhibition test in Experimental Example 2-2-3.

The results are shown in FIG. 3 and Table 6A. FIG. 3 is one of the figures showing the results of the colony formation inhibition test, and shows the results of the colony formation rate test when cells were cultured for 7 days in culture solutions having various concentrations of alginate sulfate B as a result of dilution of alginate sulfate B at a starting concentration of 0.1 mg/ml obtained by diluting the FBS-added cell culture solution containing alginate sulfate B at a starting concentration of 0.1 mg/ml stepwise with an FBS-added cell culture solution not containing alginate sulfate. In FIG. 3, the solution dilution degree (%) on the horizontal axis indicates the dilution degree of alginate sulfate 13 when the concentration of alginate sulfate B of a starting concentration of 0.1 mg/ml is defined as 100%. For example, the solution dilution degree 10% means a concentration, of alginate sulfate B, which is 10% of the starting concentration of alginate sulfate B of 0.1 mg/ml, i.e., is equal to 0.01 mg/ml. Black triangle (▲) marks and the continuous line indicate the results of Comparative control 1. The colony formation rate of 100% is a reference point when the result of Comparative control 2 is defined as 100%. Black diamond (♦) marks and the continuous line indicate the colony formation rates of cells (experimental group) cultured for 7 days in an FRS-added cell culture solution containing alginate sulfate B at concentrations diluted stepwise from the starting concentration of 0.1 mg/ml as 100%.

As shown in FIG. 3, regarding the cells cultured in a normal FBS-added cell culture solution, both the cells suspended with alginate sulfate B (Comparative control 1, experimental group), and the cells suspended by the ordinary trypsin method (Comparative control 2) adhered and formed colonies within 24 hours as usual, and no difference in the number of colonies formed was recognized between these cells (the colony formation rate of Comparative control 1 was close to the baseline of 100%).

When alginate sulfate B was diluted with a cell culture solution (experimental group), cells failed to adhere and failed to proliferate as evidenced by the colony formation rate of 6 to 14% when the concentration of alginate sulfate was 0.00625 mg/ml (namely, 6.25% when the alginate sulfate B at a starting concentration of 0.1 mg/ml is defined as 100%, that is equal to 0.00625 mg/ml) or more. However, when the concentration of alginate sulfate was 0.001 mg/ml, the cells adhered within 24 hours as usual, and the colony formation rate rapidly increased to 90% or more, revealing that the cells proliferated as usual as in Comparative control 1.

The same experimental results were obtained when alginate sulfates A, C were used in place of alginate sulfate B.

Table 6A shows the results of colony formation 50% inhibitory concentrations. For alginate sulfates A to B, the relationship between the colony formation rate and the concentration of alginate sulfate shown in FIG. 3 was determined, and a colony formation 50% inhibitory concentration was calculated from the obtained relationship. As a result, the colony formation 50% inhibitory concentration was between 0.00625 mg/ml and 0.001 mg/ml in alginate sulfate B. The same experimental results were obtained in alginate sulfate A and alginate sulfate C. The colony formation 50% inhibitory concentrations ranged from 0.01 to 0.00625 mg/ml for both cases.

TABLE 6A

| | Colony formation 50% inhibitory concentration (mg/ml) |
|---|---|
| Alginate sulfate A | 0.01 to 0.00625 |
| Alginate sulfate B | 0.00625 to 0.001 |
| Alginate sulfate C | 0.01 to 0.00625 |

These revealed that the cells detached and suspended with alginate sulfates A to C awaken from dormancy, re-adhere to the scaffold, and proliferate when the cells are transferred into a normal FBS-added cell culture solution and cultured under normal conditions (Comparative control 1), or the alginate sulfates A to C are diluted to the concentrations of 0.01 to 0.00625 mg/ml.

Experimental Example 2-2-4

By applying the colony formation inhibition test described in ISO 10993-5 (Biological evaluation of medical devices Part 5: Tests for vitro cytotoxicity), the concentration of alginate sulfate at which the cells that are made dormant by alginate sulfate (Suspension and dormancy of cells by alginate sulfate are not necessarily identical, and cells are suspended at higher concentrations, whereas cells are dormant but are not suspended at lower concentrations) awaken from the dormant state and resume the proliferation was examined. The experimental method is generally the same as that of [Experimental Example 2-2-3] and is as follows. The cells used in the experiment were a highly metastatic strain of mouse B-16 malignant melanoma.

The culture solution of the laboratory dish containing cells adhered to the laboratory dish in the FBS-added cell culture solution was replaced by an FBS-added cell culture solution containing alginate sulfate A-3 at a starting concentration of 1 mg/ml or alginate sulfate A at a starting concentration of 0.1 mg/ml to temporarily make the cells dormant. Next, a normal (namely, not containing alginate sulfate) FBS-added cell culture solution was added to the cell culture solution to adjust the concentration of alginate sulfate to the conditions diluted stepwise from the alginate sulfate concentration (the starting concentration is referred to as 1-fold dilution) to 1000-fold dilution. In cell culture solutions adjusted to the above conditions, cells were cultured under normal culture conditions (37° C., humidity 100%, carbon dioxide gas concentration 5%) for 7 days.

For these cells (experimental group), whether or not cell proliferation occurred as usual in the same manner as in Comparative controls 1-2, 1-3 and Comparative control 2-2 was observed. The degree of cell proliferation was examined by calculating the number of colonies formed after 7 days, and comparing by a method conforming to the above-described colony formation inhibition test.

As Comparative control 1-2, the culture solution of the laboratory dish containing cells adhered to the laboratory dish in the FBS-added cell culture solution was replaced by an FBS-added cell culture solution containing 1 mg/ml alginate sulfate A-3 or 0.1 mg/ml alginate sulfate A to temporarily make the cells dormant, and then the resultant cell culture solution was replaced by a normal (namely, not containing alginate sulfate) FBS-added cell culture solution. Following this operation, cells were cultured under normal culture conditions (37° C., humidity 100%, carbon dioxide gas concentration 5%) for 7 days.

As Comparative control 1-3, cells that were temporarily made dormant with 0.1 mg/ml of alginate sulfate A were used in the same manner as in the Comparative control 1-2, and then the cell culture solution was transferred to an FBS-added cell culture solution containing normal alginate sulfate (namely, non-sulfated alginic acid) at a concentration of 20 mg/ml. Then, the cells were cultured for 7 days under normal culture conditions (37° C., humidity 100%, carbon dioxide gas concentration 5%).

As Comparative control 2-2, cells suspended by the ordinary trypsin method were used. These cells were transferred to a normal FBS-added cell culture solution, and cultured under normal culture conditions (37° C., humidity 100%, carbon dioxide gas concentration 5%) for 7 days. For Comparative controls 1-2, 1-3, 2-2, it was confirmed that cell proliferation occurred as usual. The cell proliferation was examined by determining the number of colonies formed after 7 days, and comparing by a method conforming to the above-described colony formation inhibition test. Thus, Comparative control 2-2 was used as a standard for a colony formation rate of 100%.

Regarding the cells cultured in a normal FBS-added cell culture solution, the cells suspended with alginate sulfate A-3 or alginate sulfate A (Comparative control 1-2), the cells suspended by the ordinary trypsin method (Comparative control 2-2), and the cells cultured in a FBS-added cell culture solution containing 20 mg/nil normal sodium alginate as Comparative control 1-3, adhered and formed colonies as usual, and no difference in the number of colonies formed was recognized between these cells, and the colony formation rates of Comparative controls 1-2, 1-3 were close to the baseline of 100%.

When alginate sulfate A-3 was diluted with a cell culture solution (experimental group), the colony formation rate was 10% or less, and cells failed to proliferate and were in a dormant state when the concentration of alginate sulfate was 0.05 mg/ml (namely, 5% when alginate sulfate at a starting concentration of 1 mg/ml is defined as 100%, that is equal to 0.05 mg/ml) or more. However, at a lower concentration of alginate sulfate A-3 of 0.01 mg/ml (namely, 1% when alginate sulfate at a starting concentration of 1 mg/ml is defined as 100%, that is equal to 0.01 mg/ml), the colony formation rate rapidly increased to 90% or more, and it was found that the cells proliferated as usual as in Comparative control 1-2.

When alginate sulfate A was diluted with a cell culture solution (experimental group), the colony formation rate was 10% or less, and cells failed to proliferate and were in a dormant state when the concentration of alginate sulfate was 0.0005 mg/ml (namely, 0.5% when alginate sulfate at a starting concentration of 0.1 mg/ml is defined as 100%, that is equal to 0.0005 mg) or more. However, at a lower concentration of alginate sulfate A of 0.0001 mg/ml or less, the colony formation rate rapidly increased to 90% or more, and it was found that the cells proliferated as usual as in Comparative control 1-2.

Table 6B shows the results of colony formation 50% inhibitory concentrations. The colony formation 50% inhibitory concentrations were calculated by the method described above. As a result, the colony-forming 50% inhibitory concentration was between 0.05 mg/ml and 0.01 mg/nil in alginate sulfate A-3. Also, the colony formation 50% inhibitory concentration (namely, concentration exhibiting the cell dormancy effect) was between 0.0005 mg/ml and 0.0001 mg/ml in alginate sulfate A.

TABLE 6B

| | Colony formation 50% inhibitory concentration (mg/ml) |
|---|---|
| Alginate sulfate A | 0.0005 to 0.0001 |
| Alginate sulfate A-3 | 0.05 to 0.01 |
| Sodium alginate | Colony formation not inhibited (concentration 20 mg/ml) |

These revealed that alginate sulfate A-3 exhibits the dormancy effect of inhibiting cell proliferation for B-16 melanoma highly metastatic strain at concentrations between 0.05 mg/ml and 0.01 mg/ml, whereas when the cells are transferred into a normal FBS-added cell culture solution and cultured under normal conditions (Comparative control 1-2) or when the concentration of alginate sulfate A-3 is diluted to a concentration of 0.01 mg/ml or less, the cells awaken from dormancy and proliferate. In the case of alginate sulfate A, the concentration at which the cell dormancy effect was exhibited fell between 0.0005 mg/ml and 0.0001 mg/ml, and at a concentration below that, the cells awakened from dormancy and started proliferating. From these results, it is considered that alginate sulfate exerts the cell dormancy effect of alginate sulfate in a wide range of degree of substitution of sulfate group even when the degree of substitution (DS) of sulfate group per monosaccharide molecule and the concentration of alginate sulfate are different, although the effect of stopping cell proliferation and causing cell dormancy differs depending on the cell type. On the other hand, it was found that normal alginic acid having no sulfate group lacks the effect of stopping cell proliferation and causing cell dormancy even at a concentration of 20 mg/ml.

As described above, from Experimental Example 2-2, it was found that by detaching and suspending cells by using alginate sulfate, it is possible to make the suspended cells dormant, and at the same time, by culturing under normal culture conditions, it is possible to awaken the suspended cells and enable the cells to re-adhere to the scaffold and proliferate. In addition, it was found that the suspended cells can be caused to awaken, re-adhere, and proliferate by setting the concentration of alginate sulfate at a predetermined range or less.

(Experimental Example 3) Cell Protective Effect By Alginate Sulfate

Experimental Example 3-1

Experimental Example 3-1-1

An experiment was performed using the same two types of cells as in Experimental Example 1. As solutions used, for example, in preserving and transporting cells, (a) a normal serum-free cell culture solution that does not contain FBS, (b) normal serum-free cell culture solutions to which alginate sulfates A to C are added to have concentrations of 0.01, 0.05, 1, 10 mg/ml, respectively, and (c) a normal FBS-added cell culture solution prepared by adding 10% FBS to a serum-free cell culture solution were prepared. To these cell culture solutions, cells suspended by the trypsin method, which is an ordinary cell detaching and suspending method, were added at a concentration of $10^6$ cells/ml, and the resultant solutions were left to stand in a room at normal temperature (22° C.) for 24 hours, and whether cells were alive or dead was determined, and rates of viable cells (average survival rate) were calculated and compared. Whether cells were alive or dead was determined by the same trypan blue excretion test and CytoRed-stained viable cell red fluorescent observation method as in Experimental Example 2-1.

Table 7A shows the results for N=4 using rat corneal epithelial cells. As shown in Table 7A, the average viability with alginate sulfate was highest at a concentration of 1 mg/ml, and the cell protective effect decreased both at higher or lower concentrations, however, the effect at a concentration from 0.01 mg/ml to 10 mg/ml was almost comparable to or higher than that in 10% FBS-added culture which is ordinarily used. Also, it was revealed that alginate sulfate B has excellent cell protective effect at any concentration, compared with alginate sulfates A, C.

TABLE 7A

| Type of adjusted solution | Concentration of alginate sulfate (mg/ml) | Average survival rate (%) |
|---|---|---|
| Serum-free cell culture solution | 0 | <30 |
| Alginate sulfate A-added serum-free cell culture solution | 0.01 | 62 |
|  | 0.05 | 67 |
|  | 1 | 78 |
|  | 10 | 60 |
| Alginate sulfate B-added serum-free cell culture solution | 0.01 | 64 |
|  | 0.05 | 69 |
|  | 1 | 85 |
|  | 10 | 66 |
| Alginate sulfate C-added serum-free cell culture solution | 0.01 | 60 |
|  | 0.05 | 65 |
|  | 1 | 70 |
|  | 10 | 60 |
| 10% FBS-added cell culture solution | 0 | 63 |

Experimental Example 3-1-2

Whether cells were alive or dead was determined and a viable cell rate was calculated, and compared in the same manner as in Experimental example 3-1-1 except that B-16 melanoma cells were used as cells, alginate sulfates A, A-2, A-3, and A-4 were used as alginate sulfate, and those prepared by adding each of these to a serum-free cell culture solution to have concentrations shown in Table 7B were used. Table 7B shows the results for N=4.

TABLE 7B

| Type of adjusted solution | Concentration of alginate sulfate (mg/ml) | Average survival rate (%) |
|---|---|---|
| Serum-free cell culture solution | 0 | <45 |
| Alginate sulfate A-added serum-free cell culture solution | 0.0001 | 70 |
| Alginate sulfate A-added serum-free cell culture solution | 0.001 | 73 |
| Alginate sulfate A-2-added serum-free cell culture solution | 0.5 | 72 |
| Alginate sulfate A-2-added serum-free cell culture solution | 50 | 82 |
| Alginate sulfate A-3-added serum-free cell culture solution | 1 | 73 |
| Alginate sulfate A-3-added serum-free cell culture solution | 50 | 84 |
| Alginate sulfate A-4-added serum-free cell culture solution | 50 | 75 |
| 10% FBS-added cell culture solution | 0 | 74 |

It was demonstrated that, when sulfate groups exist at a sufficient concentration by increasing the concentration of alginate sulfate in the adjusted solution, the cell protective effect is exhibited not only with alginate sulfate A but also with alginate sulfate A-2 having a lower DS than alginate sulfate A, alginate sulfate A-3 having a still lower DS, and alginate sulfate A-4 having a further lower DS. Furthermore, it was found that the effect differs depending on the type of cell used in that case. That is, it was found that alginate sulfates with a wide range of degree of substitution exhibit the cell protective effect, although the concentration of alginate sulfate at which the cell protective effect appears differs depending on the type of cell.

Experimental Example 3-2

Experimental Example 3-2-1

The experiment was performed in the same manner as in Experimental Example 3-1-1 except that the condition of leaving to stand at normal temperature for 24 hours was replaced by leaving to stand in a refrigerated condition at 4° C. for 120 hours. The results are shown in Table 8A. Table 8A shows the results for N=4 using Chinese hamster fibroblasts.

TABLE 8A

| Type of adjusted solution | Concentration of alginate sulfate (mg/ml) | Average survival rate (%) |
|---|---|---|
| Serum-free cell culture solution | 0 | <20 |
| Alginate sulfate A-added serum-free cell culture solution | 0.01<br>0.05<br>1<br>10 | 60<br>62<br>73<br>61 |
| Alginate sulfate B-added serum-free cell culture solution | 0.01<br>0.05<br>1<br>10 | 60<br>66<br>77<br>60 |
| Alginate sulfate C-added serum-free cell culture solution | 0.01<br>0.05<br>1<br>10 | 62<br>66<br>69<br>58 |
| 10% FBS-added cell culture solution | 0 | 60 |

The same result was obtained even when the type of cell was changed. Further, the same result was obtained even when cells were preserved in a freezing condition (minus 30° C.) for 7 days and then thawed and used.

Experimental Example 3-2-2

The experiment was performed in the same manner as in Experimental Example 3-1-2 except that the condition of leaving to stand at normal temperature for 24 hours was replaced by leaving to stand in a refrigerated condition at 4° C., for 120 hours. The results are shown in Table 8B. Table 8B shows the results for N=4.

TABLE 8B

| Type of adjusted solution | Concentration of alginate sulfate (mg/ml) | Average survival rate (%) |
|---|---|---|
| Serum-free cell culture solution | 0 | <40 |
| Alginate sulfate A-added serum-free cell culture solution | 0.0001 | 64 |
| Alginate sulfate A-added serum-free cell culture solution | 0.001 | 68 |
| Alginate sulfate A-2-added serum-free cell culture solution | 0.5 | 65 |
| Alginate sulfate A-2-added serum-free cell culture solution | 50 | 76 |
| Alginate sulfate A-3-added serum-free cell culture solution | 1 | 78 |
| Alginate sulfate A-3-added serum-free cell culture solution | 50 | 71 |
| Alginate sulfate A-4-added serum-free cell culture solution | 50 | 66 |
| 10% FBS-added cell culture solution | 0 | 70 |

Likewise with the cell protective effect when the cells were left to stand at room temperature for 24 hours, it was demonstrated that, when sulfate groups exist at a sufficient concentration by increasing the concentration of alginate sulfate in the adjusted solution, the cell protective effect is exhibited not only with alginate sulfate A but also with alginate sulfate A-2 having a lower DS than the alginate sulfate A, alginate sulfate A-3 having a still lower DS, and alginate sulfate A-4 having a further lower DS. Furthermore, it was found that the effect differs depending on the type of cell used in that case. That is, it was found that alginate sulfate in a wide range of degree of substitution of sulfate group exhibits the cell protective effect, although the concentration of alginate sulfate at which the cell protective effect appears differs depending on the type of cell.

Experimental Example 3-3

Experimental Example 3-3-1

Whether cells were alive or dead was determined, and a viable cell rate was calculated and compared in the same manner as in Experimental example 3-1-1 except that alginate sulfate A-S was used as alginate sulfate, those prepared by adding the alginate sulfate to a serum-free cell culture solution so as to have concentrations shown in Table 9A were used, and the cells were left to stand in a room at a normal temperature (22° C.) for 24 hours and 120 hours. Table 9B shows the results for N=3. The type of cell is rat corneal epithelial cells.

TABLE 9A

| Type of adjusted solution | Concentration of alginate sulfate (mg/ml) | Average survival rate (%) 24 hours | Average survival rate (%) 120 hours |
|---|---|---|---|
| Serum-free cell culture solution | — | 52 | 34 |
| Alginate sulfate A-5-added serum-free cell culture solution | 5<br>20<br>40 | 62<br>70<br>75 | 44<br>49<br>60 |
| 10% FBS-added cell culture solution | — | 64 | 49 |

Experimental Example 3-3-2

The experiment was performed in the same manner as in Experimental Example 3-3-1 except that the condition of leaving to stand at normal temperature (22° C.) for 24 hours was replaced by leaving to stand in a refrigerated condition at 4° C. for 24 hours and 120 hours. The results are shown in Table 9B. Table 9B shows the results for N=3.

TABLE 9B

| Type of adjusted solution | Concentration of alginate sulfate (mg/ml) | Average survival rate (%) 24 hours | Average survival rate (%) 120 hours |
|---|---|---|---|
| Serum-free cell culture solution | — | 70 | 58 |
| Alginate sulfate A-5-added serum-free cell culture solution | 5<br>20<br>40 | 71<br>77<br>83 | 63<br>67<br>72 |
| 10% FBS-added cell culture solution | — | 82 | 65 |

As described above, alginate sulfate can prevent cell death comparably or better than FBS even when cells are left to stand under predetermined conditions, regardless of the viscosity type (degree of polymerization) of the alginate sulfate, and it can be seen that alginate sulfate has a cell protective effect. That is, it was found that alginate sulfate can be substituted for FBS and an autologous serum. When the cells after preservation are cultured in this way under normal culture conditions, they re-adhere and proliferate in the same manner as shown in Experimental Example 2.

Experimental Example 3-4 Cell Protective Effect of Alginate Sulfate in Extracellular Fluid Replacement Solution Experimental Example 3-4

Rat corneal cells were used as cells. Experiments were conducted using the most commonly used lactated Ringer's solution (Lactated Ringer's injection, available from Fuso Pharmaceutical Industries, Ltd.) as an extracellular fluid replacement solution. (a) Lactated Ringer's solution alone without FBS, (b) lactated Ringer's solution to which alginate sulfate A or alginate sulfate B is added in a concentration of 0.5, 2.5, or 5 mg/ml, and (c) lactated Ringer's solution to which 10% FBS is added (hereinafter, 10% FBS-added lactated Ringer's solution) were prepared. To these solutions, cells suspended by the trypsin method, which is an ordinary cell detaching and suspending method, were added at a concentration of $10^6$ cells/ml, and the solutions were left to stand in a room at normal temperature (22° C.) for 24 hours. Whether cells were alive or dead was determined, and rates of viable cells were calculated and compared. Whether cells were alive or dead was determined by the same trypan blue excretion test and CytoRed-stained viable cell red fluorescent observation method as in Experimental Example 2-1. The results are shown in Table 10A.

TABLE 10A

| Type of adjusted solution | Concentration of alginate sulfate (mg/ml) | Average survival rate (%) |
|---|---|---|
| Lactated Ringer's solution | 0 | <40 |
| Alginate sulfate A-added lactated Ringer's solution | 0.5 | 66 |
| | 2.5 | 82 |
| | 5 | 69 |
| Alginate sulfate B-added lactated Ringer's solution | 0.5 | 70 |
| | 2.5 | 87 |
| | 5 | 74 |
| 10% FBS-added lactated Ringer's solution | 0 | 67 |

Experimental Example 3-4-2

The experiment was performed in the same manner as in Experimental Example 3-4-1 except that Chinese hamster fibroblasts were used as cells, and the condition of leaving to stand at normal temperature for 24 hours was replaced by leaving to stand in a refrigerated condition at 4° C. for 120 hours. The results are shown in Table 10B. Table 10B shows the results for N=3.

TABLE 10B

| Type of adjusted solution | Concentration of alginate sulfate (mg/ml) | Average survival rate (%) |
|---|---|---|
| Lactated Ringer's solution | 0 | <35 |
| Alginate sulfate A-added lactated Ringer's solution | 0.5 | 61 |
| | 2.5 | 69 |
| | 5 | 64 |
| Alginate sulfate B-added lactated Ringer's solution | 0.5 | 70 |
| | 2.5 | 76 |
| | 5 | 65 |
| 10% FBS-added lactated Ringer's solution | 0 | 60 |

The same result was obtained even when cells were preserved in a freezing condition (minus 30° C.) for 7 days and then thawed and used.

As shown in Tables 10A, B, it was found that by containing alginate sulfate, cell death can be prevented comparably or better than the case of adding 10% FBS and the cell protective effect is exerted even when the extracellular fluid replacement solution is used. That is, it was found that alginate sulfate is added, thereby allowing an extracellular fluid replacement solution to be used as a substitute for a culture solution. When the cells after preservation are cultured in this way under normal culture conditions, they re-adhere and proliferate in the same manner as shown in Experimental Example 2.

Experimental Example 4 Effect of Activating Suspended Cells By Combination of Alginate Sulfate and Activator Experimental Example 4-1

An experiment was performed using two types of cells as in Experimental Example 1 and alginate sulfates A to C obtained in production examples. Further, as the activator for alginate sulfate, an aqueous solution of calcium chloride as a calcium ion solution, a cloth piece in which a calcium ion supplier was impregnated or carried on a surface, or calcium phosphate powder was used. Here, a chelated calcium preparation was used as the calcium supplier.

Alginate sulfate in the culture solution was reacted with an activator by a method of dropping a 5% calcium chloride solution as a calcium ion solution little by little into a FBS-added cell culture solution containing $10^6$ cells/ml of cells suspended with a 1 mg/ml alginate sulfate aqueous solution, while stirring the cell culture solution gently and slowly, or a method of leaving (a) calcium phosphate powder or (b) a cloth piece (3 mm×3 mm) in which a calcium ion supplier is impregnated or carried on a surface, to stand in a culture dish, and gently and slowly pouring a cell culture solution that contains alginate sulfate containing cells suspended by alginate sulfate.

In the comparative control, the treatment was performed in the same manner as described above except that a calcium ion source was not used. That is, the treatment was performed in the same manner by using distilled water instead of 5% calcium chloride, without using calcium phosphate powder, and using a cloth piece in which a calcium ion supplier is not impregnated or carried on a surface.

After performing the above operation, whether the suspended cells adhered to the scaffold within 1 minute was examined. Cell adhesion was determined in the following manner. Cells were gently and slowly washed by replacing the culture solution by the same fresh culture solution, and whether the cells were washed away was observed under a microscope, and further, the adhered cells were observed by viable cell red fluorescent observation using the CytoRed-stained viable cell red fluorescent observation method that also allows observation of cells in a stereoscopic view under a fluorescence microscope.

Figure 4A:
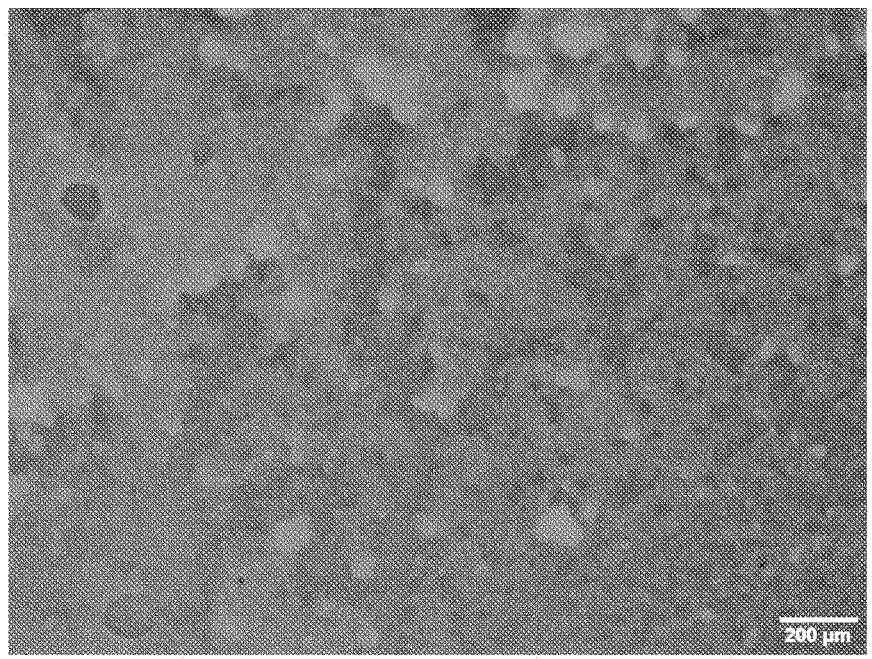
FIG. 4A shows a fluorescent micrograph image of an experimental example using Chinese hamster fibroblasts and suspended cells obtained with the later-described alginate sulfate A, and using calcium phosphate powder as an activator in Experimental Example 4-1.
Figure 4B:
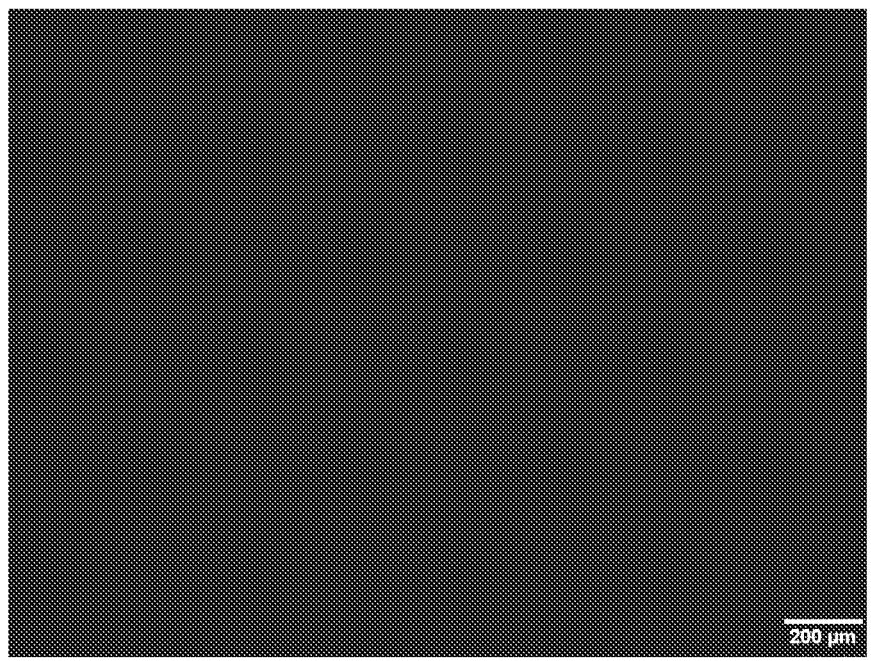
FIG. 4B shows a fluorescent micrograph image of a comparative control in which the experiment was conducted under the same conditions as in the experimental example showing the image of FIG. 4A except that calcium phosphate powder was not used.

The results are shown in FIGS. 4A and 4B. FIG. 4A shows a fluorescent micrograph image of an experimental example using Chinese hamster fibroblasts and suspended cells obtained with alginate sulfate B, and using calcium phosphate powder as an activator. In FIG. 4A, the entire image assumes a red color, and on the drawing, the stronger the red color, the whiter it is. FIG. 4B shows a fluorescent micrograph image of a comparative control in which the experiment was conducted under the same conditions with the experimental example showing the image of FIG. 4A except that calcium phosphate powder was not used. In FIG. 4B, the entire imaging assumes deep black.

As a result of the experiment, alginate sulfate gelated within 1 minute both in the case where the 5% calcium chloride solution was added dropwise as a calcium ion solution, and in the case where calcium phosphate powder or a cloth piece in which a calcium ion supplier was impregnated or carried on the surface was placed in the laboratory dish. Adhesion of cells to the gelated alginic acid was Observed. On the surface of the bottom of the laboratory dish where calcium phosphate powder was placed (FIG. 4A) and the surface of the cloth piece in which the calcium ion supplier was impregnated or carried on the surface, adhesion of an infinite number of viable cells via the gelated alginate sulfate was observed by red staining in viable cell red fluorescent observation. These cells were not washed away even after gentle washing. On the other hand, in the laboratory dish on which calcium phosphate powder was not placed (FIG. 4B) or in the cloth piece not carrying a calcium ion supplier, red staining of fibers was not observed, revealing the lack of adhesion of viable cells.

Regardless of the types of alginate sulfate, cells, and activator, the entire image of the fluorescence microscope assumed red as with the result shown in FIG. 4A Experimental Example 4-2

Whether the re-adhered cells obtained in Experimental Example 4-1 proliferated was examined. That is, the alginate sulfate gel itself to which the cells adhered and the calcium phosphate powder or the cloth piece to which an infinite number of viable cells adhere via the gelated alginate sulfate were transferred to a normal (namely, not containing alginate sulfate) FBS-added cell culture solution, and cultured for 4 days under normal culture conditions. This was observed by CytoRed-stained viable cell red fluorescent observation and compared with the state at the start of culture.

Figure 5A:
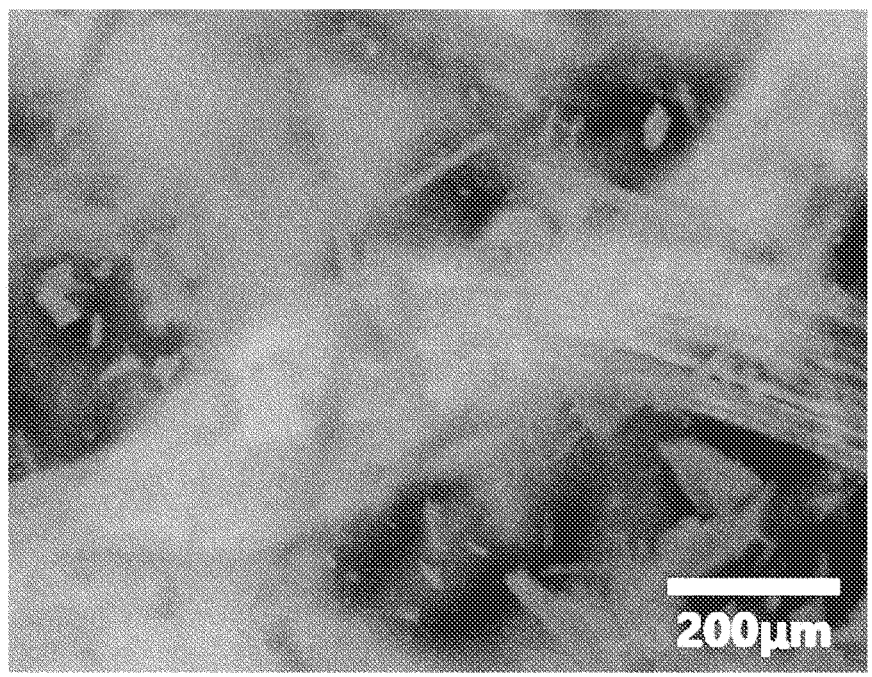
FIG. 5A shows a fluorescent micrograph image after culturing for 4 days in an experimental example using Chinese hamster fibroblasts and suspended cells obtained with the later-described alginate sulfate A, and using a cloth piece carrying a calcium supplier as an activator in Experimental Example 4-2.
Figure 5B:
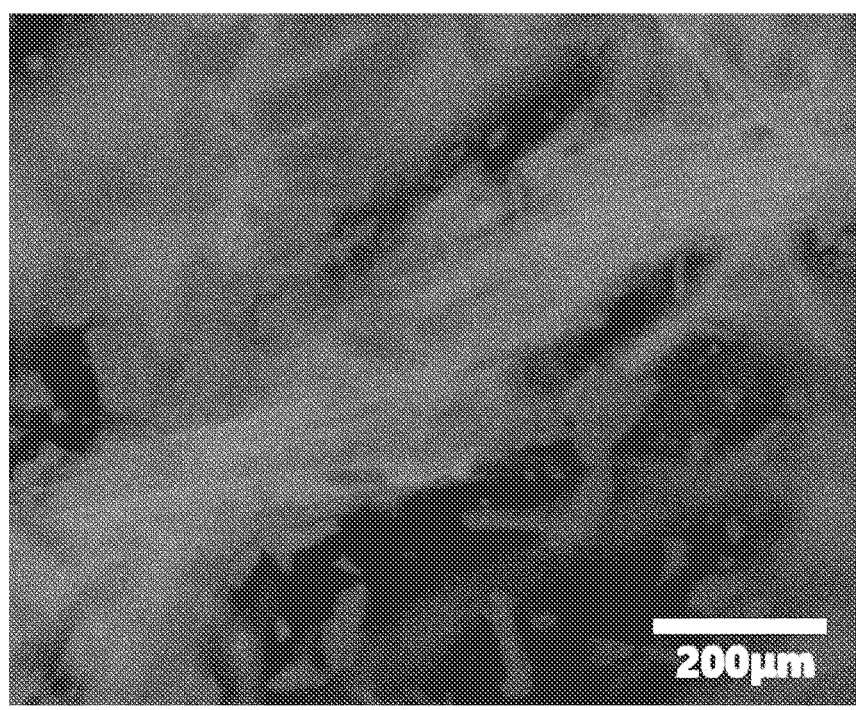
FIG. 5B shows a fluorescent micrograph image immediately before starting the culture in the experimental example of FIG. 5A.

The results are shown in FIGS. 5A and 5B. FIG. 5A shows a fluorescent micrograph image after culturing for 4 days in an experimental example using suspended cells of Chinese hamster fibroblasts obtained with alginate sulfate B, and using a cloth piece carrying a calcium supplier as an activator as in Experimental Example 4-1, and FIG. 5B shows a fluorescent microscopic image immediately before starting culture. In FIGS. 5A and 5B, the part corresponding to fibers forming the cloth piece assumes a red color, and on the drawing, the stronger the red color, the whiter it is.

As a result of the experiment, both in the case where a 5% calcium chloride solution was added dropwise as a calcium ion solution, and in the case where calcium phosphate powder or a cloth piece in which a calcium ion supplier was impregnated or carried on the surface, was placed in the laboratory dish, fluorescence strongly emitting red light was observed on the surface after culture, compared with before culture, revealing that cells adhered via alginate sulfate proliferated. As shown in FIG. 5A, red fluorescence is strong because cells proliferate and the number of viable cells is large during the culture period of 4 days, whereas as shown in FIG. 5B, the red fluorescence is weak because the number of viable cells is not yet sufficiently large immediately before culture.

Regardless of the types of alginate sulfate, cells, and activator, in the fluorescence microscopic image, the part of fibers forming the cloth piece assumed strong red after culture of 4 days compared with before start of the culture as with the result shown in FIGS. 5A and 5B.

Thus, it was found that by gelating alginate sulfate with the activator containing calcium ions, the suspended cells can be rapidly adhered to the scaffold, and easily collected by adhesion, and then proliferate by culture under normal culture conditions. Specifically, by adding cells that are detached and suspended to an alginate sulfate-added cell culture solution to let the alginate sulfate and the suspended cells coexistent, and further letting an activator coexistent with the alginate sulfate, the alginate sulfate is gelated by the activator, and the suspended cells are captured by the gelated alginate sulfate. Then, as described above, the suspended cells in a dormant state are awakened by the alginate sulfate, and adhesion of the suspended cells is accelerated by the gel-like carrier of alginate sulfate to start proliferation. Thus, a set reagent capable of successfully activating suspended cells can be established by using a combination of alginate sulfate and an activator.

Experimental Example 5 Cell Dormancy Effect Maintaining Undifferentiated State By Alginate Sulfate The cell dormancy effect by alginate sulfate was considered according to the effect of preventing differentiation by maintaining the cells in an undifferentiated state, as an index. As the cells, undifferentiated mesenchymal stem cells derived from rat subcutaneous fat (hereinafter referred to as "ADSCs") (available from COSMO BIO Co., Ltd, MSA01C) were used.

In a non-added control group, Adipose Tissue-derived Mesenchymal Stem Cell (hereinafter referred to as "AMSC") Growth Medium, Rat (available from COSMO BIO Co., Ltd., MSA-GM) was used as a cell culture solution; in a 10% FBS-added group, AMSC Growth Medium, Rat to which FBS is added to be 10% was used; and in an alginate sulfate-added group, AMSC Growth Medium, Rat to which alginate sulfate is added to be 2.5 mg/ml was used as a cell preservation liquid. After adding ADSCs to these so that the concentration was $10^5$ cells/ml each, they were left to stand for 48 hours under refrigerated conditions at 4° C. These cells were detached and suspended using the ordinary trypsin method, and the degree of differentiation of these cells was evaluated and compared by flow cytometry. The method followed the method described in Masoumeh Fakhr Taha, Vahideh Hedayati "Isolation, identification and multipotential differentiation of mouse adipose tissue-derived stem cells" Tissue and Cell 42 (2010) 211-216. The evaluation was made according to CD29 and CD44 as undifferentiation markers and CD11b, CD31 and CD45 as markers of differentiation into mesenchymal cells. The results are shown in Table 11.

TABLE 11

| Marker | | Alginate sulfate-added group | 10% FBS-added group | Non-added control group |
|---|---|---|---|---|
| Positivity rate of marker (%) | CD29 | 42 | 25.3 | 26.9 |
| | CD44 | 43.1 | 10.4 | 19.4 |
| | CD11b | 32.5 | 56.5 | 54.5 |
| | CD31 | 3.3 | 9.6 | 11.8 |
| | CD45 | 1.9 | 5.1 | 5 |

As shown in Table 11, the positivity rates in the two types of undifferentiation markers (CD29 and CD44) were significantly higher in the alginate sulfate-added group, than in the 10% FBS-added group or in the non-added control group. On the other hand, the positivity rates in the three types of differentiation markers (CD11b, CD31, and CD45) were all clearly lower in the alginate sulfate-added group than in the 10% FBS-added group or in the non-added control group. Thus, it was revealed that alginate sulfate makes cells in an undifferentiated state dormant to prevent differentiation, while FBS equally having a cell protective effect and a normal non-added cell culture solution allow and do not prevent differentiation of cells.

As described above, as shown in Experimental Examples 1 to 5, alginate sulfate can easily realize detaching and suspending cells, making cells dormant, and protecting cells, while alginate sulfate without cytotoxicity can easily realize awakening of cells from a dormant state, and re-adhesion and re-proliferation because of lack of cytotoxicity. Furthermore, by combining alginate sulfate with an activator, it is possible to freely control the collection of suspended cells, and resumption of adhesion and proliferation of cells (planting). Therefore, the combination is extremely effective as a set reagent of a cell treatment agent and an activator agent for use in a very simple and safe cell detachment and suspension, storage and transportation (in particular, as a cell protective agent alternative to FBS, human serum, etc.), and planting.

The invention claimed is:

1. A cell treatment agent comprising alginate sulfate as an active ingredient and at least one selected from the group consisting of a cell culture solution, an extracellular fluid replacement solution, and a maintenance infusion,
wherein in the alginate sulfate, an alginate sulfate with a sulfate group introduced into a carbon atom at position 6 occupies more than 10% of a total of the alginate sulfate to achieve high treatment capacities for cells.

2. The cell treatment agent according to claim 1, wherein an amount of the alginate sulfate with a sulfate group introduced into the carbon atom at position 6 is 20% or more of a total of the alginate sulfate.

3. The cell treatment agent according to claim 1, wherein an amount of the alginate sulfate with a sulfate group introduced into the carbon atom at position 6 is 50% or more of a total of the alginate sulfate.

4. The cell treatment agent according to claim 1, wherein an amount of the alginate sulfate with a sulfate group introduced into the carbon atom at position 6 is 80% or more of a total of the alginate sulfate.

5. A method for detaching a cell from a scaffold, wherein the scaffold is a living tissue or a culture substrate, and wherein the cell and scaffold are in a cell culture solution, the method comprising adding the cell treatment agent according to claim 1 to the cell culture solution.

6. A method for making a cell dormant, wherein the cell is in a tissue or in a cell culture, and the tissue or cell culture are in a cell culture solution, the method comprising adding the cell treatment agent according to claim 1 to the cell culture solution.

7. A method for maintaining viability of a cell, wherein the cell is in a tissue or in a cell culture, comprising providing the cell in the cell treatment agent according to claim 1.

8. A method for maintaining a cell in an undifferentiated state, comprising providing the cell in the cell treatment agent according to claim 1.

9. The cell treatment agent according to claim 1, wherein the cell treatment agent is a liquid for cell preservation, tissue preservation, or organ preservation.

10. A set reagent for activation of a suspended cell or a dormant cell, the set reagent being a combination reagent of the cell treatment agent according to claim 1 and an activator containing a polyvalent cation.

* * * * *